(12) United States Patent
Huang et al.

(10) Patent No.: US 11,779,284 B2
(45) Date of Patent: Oct. 10, 2023

(54) BASAL METABOLISM ESTIMATION DEVICE, BASAL METABOLISM ESTIMATION SYSTEM, BASAL METABOLISM ESTIMATION METHOD, AND PROGRAM

(71) Applicant: NEC Corporation, Tokyo (JP)

(72) Inventors: Chenhui Huang, Tokyo (JP); Kenichiro Fukushi, Tokyo (JP); Yusuke Sekiguchi, Sendai (JP); Haruki Yaguchi, Sendai (JP); Keita Honda, Sendai (JP); Shinichi Izumi, Sendai (JP); Dai Owaki, Sendai (JP)

(73) Assignee: NEC CORPORATION, Tokyo (JP)

( * ) Notice: Subject to any disclaimer, the term of this patent is extended or adjusted under 35 U.S.C. 154(b) by 153 days.

(21) Appl. No.: 17/364,150

(22) Filed: Jun. 30, 2021

(65) Prior Publication Data

US 2022/0000434 A1    Jan. 6, 2022

(30) Foreign Application Priority Data

Jul. 3, 2020   (JP) ................................ 2020-115942

(51) Int. Cl.
*A61B 5/00* (2006.01)
*A61B 5/103* (2006.01)
*G16H 40/63* (2018.01)

(52) U.S. Cl.
CPC .......... *A61B 5/7278* (2013.01); *A61B 5/1038* (2013.01); *A61B 5/4866* (2013.01);
(Continued)

(58) Field of Classification Search
CPC ... A61B 5/7278; A61B 5/1038; A61B 5/4866; A61B 5/6807; A61B 5/7267;
(Continued)

(56) References Cited

U.S. PATENT DOCUMENTS

2007/0021421 A1*  1/2007  Hampton ............. A61K 31/138
                                                514/237.5
2017/0055880 A1*  3/2017  Agrawal .................. A43B 3/38
(Continued)

FOREIGN PATENT DOCUMENTS

CN    108186024    *  6/2018   ............ A61B 5/746
JP    2018-505759 A    3/2018
WO    2016/110804 A1   7/2016

OTHER PUBLICATIONS

Viteckova et al., "Gait symmetry measures: A review of current and prospective methods", Biomedical Signal Processing and Control, 42, 89-100 (Year: 2018).*

(Continued)

*Primary Examiner* — Eric F Winakur
*Assistant Examiner* — Jonathan Drew Moroneso
(74) *Attorney, Agent, or Firm* — Sughrue Mion, PLLC

(57) ABSTRACT

A basal metabolism estimation device includes: at least one memory configured to store instructions; and at least one processor configured to execute the instructions to: acquire first measurement data related to a left foot and second measurement data related to a right foot; identify a starting timing and an ending timing of a stance phase of each of the left and right feet based on the first and second measurement data; calculate a stride time for one cycle of movement of one of the feet during walking and a degree of asymmetry between the first measurement data in the stance phase of the left foot and the second measurement data in the stance phase of the right foot; and estimate basal metabolism based on the stride time and the degree of asymmetry.

11 Claims, 14 Drawing Sheets

(52) U.S. Cl.
CPC ............ *G16H 40/63* (2018.01); *A61B 5/6807* (2013.01); *A61B 5/7267* (2013.01); *A61B 2562/04* (2013.01)

(58) Field of Classification Search
CPC .... A61B 2562/04; G16H 40/63; G16H 50/20; G16H 50/30; G16H 40/67
See application file for complete search history.

(56) References Cited

U.S. PATENT DOCUMENTS

| | | | |
|---|---|---|---|
| 2017/0203154 A1* | 7/2017 | Solinsky | A63B 69/0028 |
| 2019/0150793 A1* | 5/2019 | Barth | A61B 5/112 |
| 2021/0187347 A1* | 6/2021 | Remsberg | A63B 71/0622 |

OTHER PUBLICATIONS

Nguyen et al., "Characterizing the relationship between step length asymmetry and metabolic rate during locomotion in post-stroke individuals" (Year: 2017).*

* cited by examiner

ID Metabolism Estimation
BASAL METABOLISM ESTIMATION DEVICE, BASAL METABOLISM ESTIMATION SYSTEM, BASAL METABOLISM ESTIMATION METHOD, AND PROGRAM This application is based upon and claims the benefit of priority from Japanese patent application No. 2020-115942, filed on Jul. 3, 2020, the disclosure of which is incorporated herein in its entirety by reference.

TECHNICAL FIELD

The present invention relates to a basal metabolism estimation device, a basal metabolism estimation system, a basal metabolism estimation method, and a program.

BACKGROUND ART

Regarding monitoring of metabolism, Published Japanese Translation No. 2018-505759 of the PCT International Publication discloses combining a wearable device such as an armband phone case with a sensor including embedded-type metabolism monitoring, and modeling metabolism by measuring heat dissipation using means such as an infrared sensor capable of characterizing diffusion and release of body heat and imaging physiological temperature and spatiotemporal activity heat.

SUMMARY

From the viewpoint of a processing load of equipment, it is preferable to be able to monitor metabolism through lighter processing without requiring complicated processing such as imaging of heat.

An object of the present invention is to provide a basal metabolism estimation device, a basal metabolism estimation system, a basal metabolism estimation method, and a program capable of resolving the problems described above.

According to a first example aspect of the present invention, a basal metabolism estimation device includes: at least one memory configured to store instructions; and at least one processor configured to execute the instructions to: acquire first measurement data related to a left foot and second measurement data related to a right foot; identify a starting timing and an ending timing of a stance phase of each of the left and right feet based on the first and second measurement data; calculate a stride time for one cycle of movement of one of the feet during walking and a degree of asymmetry between the first measurement data in the stance phase of the left foot and the second measurement data in the stance phase of the right foot; and estimate basal metabolism based on the stride time and the degree of asymmetry.

According to a second example aspect of the present invention, a basal metabolism estimation system includes: at least one sensor that measures first data related to a left foot and second data related to a right foot; at least one memory configured to store instructions; and at least one processor configured to execute the instructions to: identify a starting timing and an ending timing of a stance phase of each of the left and right feet based on the first and second data; calculate a stride time for one cycle of movement of one of the feet during walking and a degree of asymmetry between the first data in stance phase of the left foot and the second data in stance phase of the right foot; and estimate basal metabolism based on the stride time and the degree of asymmetry.

According to a third example aspect of the present invention, a basal metabolism estimation method includes: acquiring first measurement data related to a left foot and second measurement data related to a right foot; identifying a starting timing and an ending timing of a stance phase of each of the left and right feet based on the first and second measurement data; calculating a stride time for one cycle of movement of one of the feet during walking and a degree of asymmetry between the first measurement data in the stance phase of the left foot and the second measurement data in the stance phase of the right foot; and estimating basal metabolism based on the stride time and the degree of asymmetry.

According to a fourth example aspect of the present invention, a program is a program for causing a computer to execute: acquiring first measurement data related to a left foot and second measurement data related to a right foot; identifying a starting timing and an ending timing of a stance phase of each of the left and right feet based on the first and second measurement data; calculating a stride time for one cycle of movement of one of the feet during walking and a degree of asymmetry between the first measurement data in the stance phase of the left foot and the second measurement data in the stance phase of the right foot; and estimating basal metabolism based on the stride time and the degree of asymmetry.

EXAMPLE EMBODIMENT

Hereinafter, example embodiments of the present invention will be described. However, the following example embodiments do not limit the invention according to the claims. In addition, all the combinations of features described in the example embodiments may not be essential for the solution of the invention.

First Example Embodiment

Figure 1:
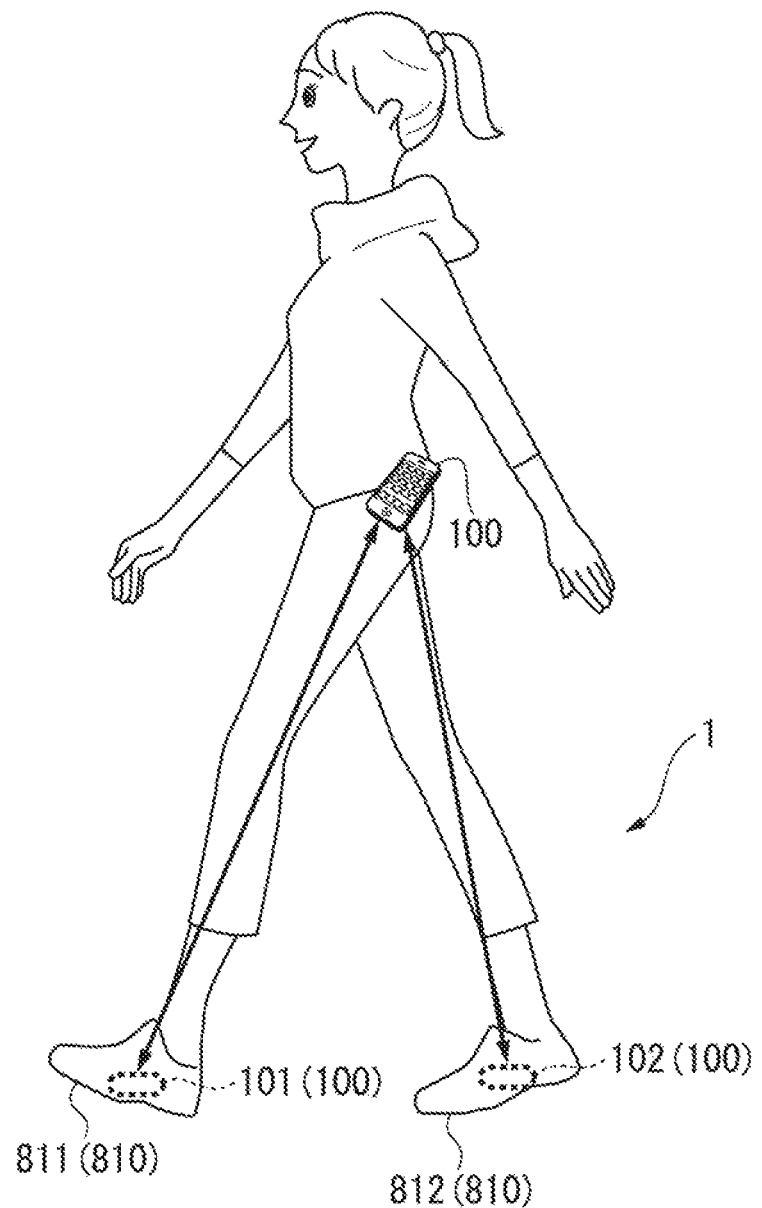
FIG. 1 is a view of a schematic constitution illustrating an example of a constitution of a device of a basal metabolism estimation system according to a first example embodiment.

FIG. 1 is a view of a schematic constitution illustrating an example of a constitution of a device of a basal metabolism estimation system according to a first example embodiment. In the constitution illustrated in FIG. 1, a basal metabolism estimation system 1 includes a left side sensor system 101, a right side sensor system 102, and a basal metabolism estimation device 200.

The basal metabolism estimation system 1 estimates basal metabolism of a basal metabolism estimation subject person. Basal metabolism denotes a metabolic rate of minimum necessary energy consumed for life support at the time of a stable state in both mind and body. A basal metabolism estimation subject person will also be simply referred to as a subject person.

Here, there is a relatedness between basal metabolism and walking, and the basal metabolism estimation system 1 estimates basal metabolism on the basis of measurement data when the subject person walks.

Figure 2:
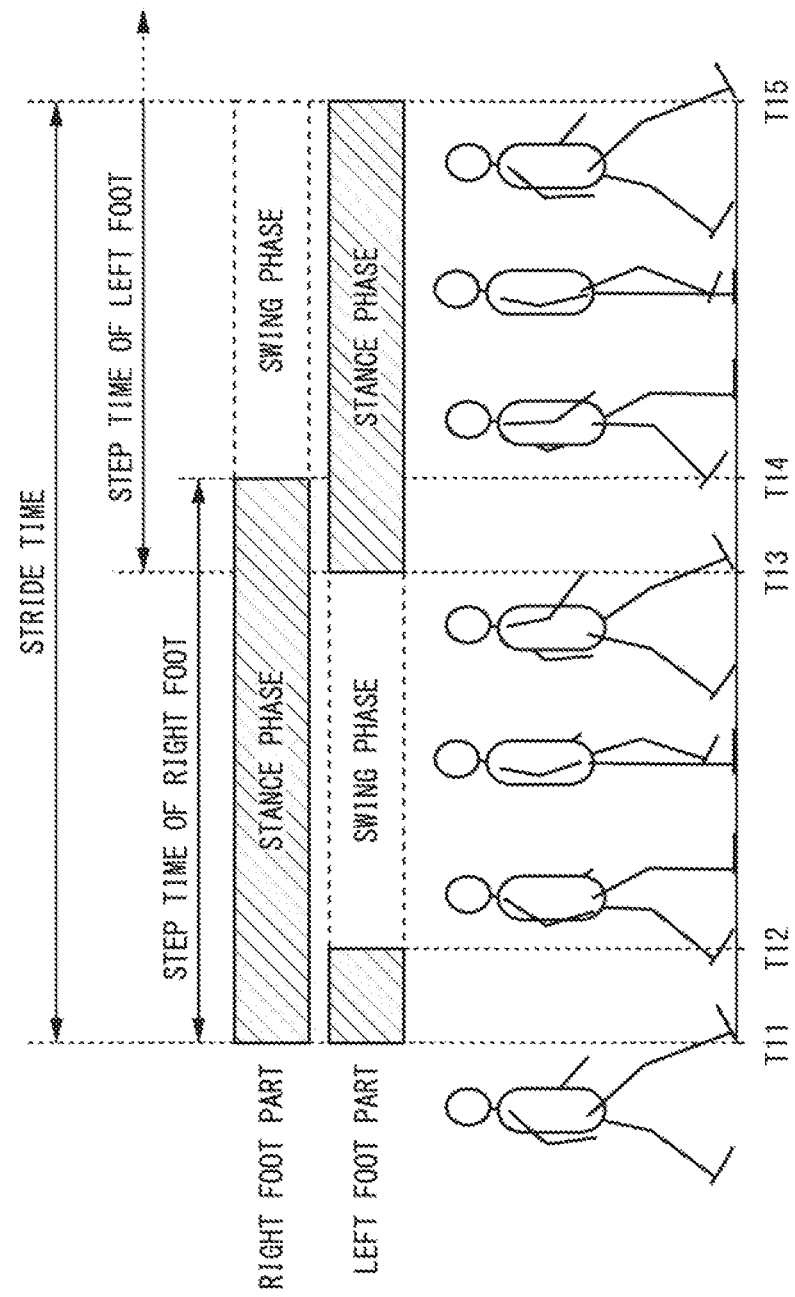
FIG. 2 is a view illustrating an example of a stride time and a step time calculated by the basal metabolism estimation system according to the first example embodiment.

FIG. 2 is a view illustrating an example of a stride time and a step time calculated by the basal metabolism estimation system 1.

FIG. 2 illustrates an example of phases of movement of the left and right feet during one walking cycle. One walking cycle is a period of a series of motions corresponding to one unit of motion repeated in walking.

One walking cycle will also be simply referred to as a walking cycle. In addition, a time taken for one walking cycle will be referred to as a stride time.

In regard to either the left or right foot, a stance phase and a swing phase are repeated at the time of walking, and a combination of one stance phase and one swing phase corresponds to one walking cycle. A stance phase is a period during which the feet are in contact with the ground surface. A swing phase is a period during which the feet leave the ground surface. A time taken for a stance phase will be referred to as a step time.

When the subject person puts on shoes, a state in which the shoe is in contact with the ground surface is equated with a state in which the foot is in contact with the ground surface. Particularly, ground contact of the shoe is regarded as ground contact of the foot. Moreover, ground contact of a heel part of the shoe is regarded as ground contact of the heel of the foot. In addition, the shoe leaving the ground is regarded as the foot leaving the ground. Moreover, a toe part of the shoe leaving the ground is regarded as the toes of the foot leaving the ground.

The horizontal axis in FIG. 2 indicates time, and FIG. 2 illustrates an example of phases of the left and right feet during a period from a time T11 to a time T15.

In the example of FIG. 2, the right foot (which will also be referred to as the right foot part) comes into contact with the ground at the time T11, the right foot leaves the ground at the time T14, and the right foot comes into contact with the ground again at the time T15. In the example of FIG. 2, when the foot comes into contact with the ground, the foot comes into contact with the ground from the heel. In addition, when the foot leaves the ground, the toes leave the ground last. For this reason, the heel of the right foot comes into contact with the ground at the time T11, and the toes of the right foot leave the ground at the time T14. The heel of the right foot comes into contact with the ground again at the time T15.

As described above, during ordinary walking, the foot comes into contact with the ground from the heel and the toes leave the ground last when the foot leaves the ground.

In the example of FIG. 2, a period from the time T11 to the time T14 corresponds to a stance phase of the right foot. A period from the time T14 to the time T15 corresponds to a swing phase of the right foot.

Therefore, a time period from the time T11 to the time T14 (T14–T11) corresponds to a step time of the right foot.

Regarding the left foot (which will also be referred to as the left foot part), the left foot leaves the ground at the time T12, and the left foot comes into contact with the ground at the time T13. Each of the period to the time T12 and the period from the time T13 corresponds to a stance phase of the left foot. A period from the time T12 to the time T13 corresponds to a swing phase of the left foot. Also regarding the left foot, the foot comes into contact with the ground from the heel, and the toes leave the ground last.

In this case, for example, a time period from when the left foot leaves the ground at the time T13 until when the left foot comes into contact with the ground next corresponds to a step time of the left foot. When the subject person repeats a walking cycle with a uniform rhythm, the sum of a time period from the time T11 to the time T12 and a time period from the time T14 to the time T15 (T12–T11+T15–T14) corresponds to a step time of the left foot.

In the example of FIG. 2, in the period from the time T11 to the time T14 which is the stance phase of the right foot and the period from the time T13 which is the stance phase of the left foot, periods from the time T13 to the time T14 temporally overlap each other. In this manner, parts of the stance phase of the right foot and the stance phase of the left foot overlap each other in walking.

In the example of FIG. 2, one walking cycle is a period from when the right foot comes into contact with the ground until the right foot comes into contact with the ground next. However, one walking cycle is not limited thereto and need only be a period from a certain phase in either the left or right foot to the next same phase in the same feet. For example, one walking cycle may be a period from when the left foot comes into contact with the ground until the left foot comes into contact with the ground again next. Alternatively, one walking cycle may be a period from when the right foot leaves the ground until the right foot leaves the ground again next.

When the subject person repeats a walking cycle with a uniform rhythm, the stride time (a time taken for one walking cycle) is approximately the same regardless of which timing a starting timing of one walking cycle is set to.

On the other hand, even when the subject person repeats a walking cycle with a uniform rhythm, a step time of the right foot and a step time of the left foot are not always the same time.

Figure 3:
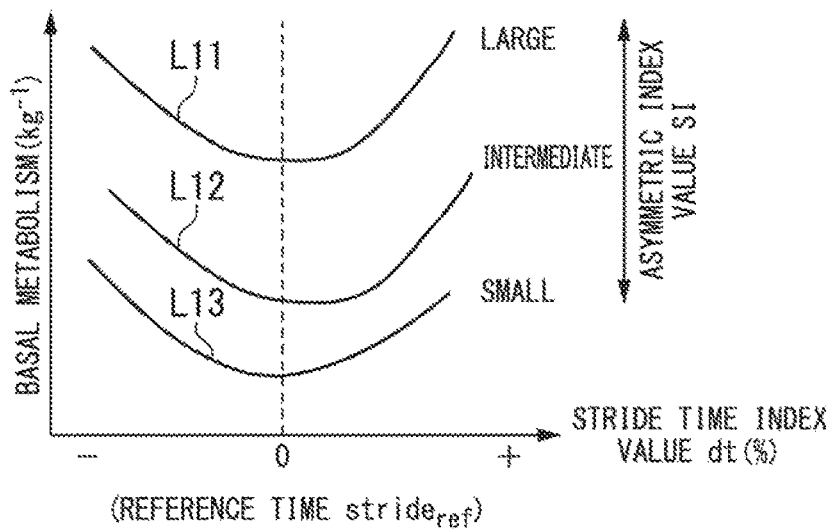
FIG. 3 is a view illustrating an example of a relatedness between basal metabolism and walking.

FIG. 3 is a view illustrating an example of a relatedness between basal metabolism and walking. The horizontal axis in the graph of FIG. 3 indicates stride time index value which is one of index values indicating stride lengths. The vertical axis indicates basal metabolism (basal metabolic rate). Regarding basal metabolism, for example, the ratio of energy consumption per kilogram of body weight to a reference value can be used. Basal metabolism will be expressed as "W".

A stride time index value is an index value indicating the length of a stride time in comparison with a reference time. A stride time index value dt is expressed by Expression (1).

$$dt = \frac{stride - stride_{ref}}{stride_{ref}} \times 100\% \quad (1)$$

The variable "stride" indicates a stride time of the subject person calculated by the basal metabolism estimation system 1. The variable "$stride_{ref}$" indicates a reference time for a stride time. A reference time for a stride time is set in advance in accordance with the age, the height, and the body weight, for example. A reference time for a stride time will also be simply referred to as a reference time.

For example, the basal metabolism estimation device 200 may read a reference time according to data such as the height and the body weight of the subject person with reference to database of reference times.

When the stride time "stride" is longer than the reference time "$stride_{ref}$", the value of the stride time index value dt becomes a positive value. On the other hand, when the stride time "stride" is shorter than the reference time "$stride_{ref}$", the value of the stride time index value dt becomes a negative value. When the stride time "stride" is equivalent to the reference time "$stride_{ref}$", the value of the stride time index value dt becomes zero.

Lines L11, L12, and L13 indicate relationships between the stride time index value dt and the basal metabolism W when a time asymmetric index value SI is relatively small, when it is an intermediate value, and when it is relatively large, respectively.

The time asymmetric index value SI is an index value indicating a degree of asymmetry in the left and right feet during a step time (a time period of a stance phase). A degree of asymmetry in the left and right feet during a step time corresponds to an example of a degree of asymmetry in the left and right feet regarding the measurement data during the stance phase. Here, asymmetry in the left and right feet regarding data denotes that data differs between the left and right feet.

Here, differing data (difference) may be a difference between magnitudes of a value of data such as an acceleration, but it is not limited thereto. For example, differing data may be a difference between lengths of a time calculated on the basis of data.

The time asymmetric index value SI is expressed by Expression (2).

$$SI = \left| \frac{step_r - step_l}{0.5 \times (step_r + step_l)} \right| \times 100\% \quad (2)$$

The variable "$step_r$" indicates a step time of the right foot. The variable "$step_l$" indicates a step time of the left foot.

In the relationship between the stride time "stride" and the basal metabolism W, the basal metabolism W is minimized when the stride time index value dt is in the vicinity of zero. Therefore, when the stride time "stride" is approximately equivalent to the reference time "$stride_{ref}$", the basal metabolism W is minimized. In addition, all of the lines L11, L12, and L13 are approximately line-symmetrical between a positive case and a negative case centering on a case in which the stride time index value dt is zero. In both the positive and negative cases, the basal metabolism W increases as the magnitude (absolute value) of the stride time index value dt increases. Therefore, in both the cases in which the stride time "stride" is longer and shorter than the reference time "$stride_{ref}$", the basal metabolism W increases as the difference between the stride time "stride" and the reference time "$stride_{ref}$" increases.

In a relationship between: the degree of asymmetry in the left and right feet during a step time; and the basal metabolism W, the basal metabolism W increases as the time asymmetric index value SI increases. Therefore, the basal metabolism W increases as a difference between a step time "$step_r$" of the right foot and a step time "$step_l$" of the left foot increases.

As in the example of FIG. 3, there is a relatedness between: the basal metabolism W; and the stride time index value dt and the time asymmetric index value SI. On the basis of this relatedness, as in Expression (3), the basal metabolism W is expressed by a function f of the stride time index value dt and the time asymmetric index value SI.

$$W = f(dt, SI) \quad (3)$$

The basal metabolism estimation device 200 may estimate (calculate) basal metabolism on the basis of Expression (3). In this case, the function f may be obtained through machine learning. Alternatively, a person such as a designer of the basal metabolism estimation system 1 may obtain the function f on the basis of statistical data, for example.

In addition, the function f may be obtained for each attribute of the subject person, such as each of the height, the body weight, and the age of the subject person. Further, the basal metabolism estimation device 200 may estimate the basal metabolism W by acquiring the function f corresponding to the attribute of the subject person.

Alternatively, Expression (3) can be approximated as Expression (4) using a function g of the stride time index value dt and a function h of the time asymmetric index value SI.

$$W = g(dt) + h(SI) \quad (4)$$

The basal metabolism estimation device 200 may estimate (calculate) basal metabolism on the basis of Expression (4). In this case, the function g and the function h may be obtained through machine learning. Alternatively, a person such as a designer of the basal metabolism estimation system 1 may obtain the function g and the function h on the basis of statistical data, for example.

In addition, the function g and the function h may be obtained for each attribute of the subject person, such as each of the height, the body weight, and the age of the subject person. Further, the basal metabolism estimation device 200 may estimate the basal metabolism W by acquiring the function g and the function h corresponding to the attribute of the subject person.

Alternatively, as described above, the stride time index value dt and the basal metabolism W have a relationship of approximately line symmetry centering on dt=0. From this, the function g(dt) can become an even function.

In addition, the time asymmetric index value SI and the basal metabolism W have a relationship of monotonic increase (positive correlation). From this, the function h(SI) can become a monotonic increase function.

For example, when a quadratic function is used as the function g(dt) and a directly proportional function (linear function) is used as the function h(SI), Expression (4) can be approximated as Expression (5).

$$W = a \times dt^2 + b \times SI \quad (5)$$

Each of a and b indicates a constant which is a real number.

The basal metabolism estimation device 200 may estimate (calculate) basal metabolism on the basis of Expression (5). In this case, a value of the coefficient a and a value of the coefficient b may be obtained through machine learning. Alternatively, a person such as a designer of the basal metabolism estimation system 1 may obtain the value of the coefficient a and the value of the coefficient b on the basis of statistical data, for example.

In addition, the value of the coefficient a and the value of the coefficient b may be obtained for each attribute of the subject person, such as each of the height, the body weight, and the age of the subject person. Further, the basal metabolism estimation device 200 may estimate the basal metabolism W by acquiring the value of the coefficient a and the value of the coefficient b corresponding to the attribute of the subject person.

Each of the left side sensor system 101 and the right side sensor system 102 includes a sensor such as an inertial measurement unit (IMU) and measures movement of each of the left foot and the right foot. Particularly, the left side sensor system 101 measures an acceleration of the left foot in a forward-rearward direction. The right side sensor system 102 measures an acceleration of the right foot in the forward-rearward direction. Here, the forward-rearward direction is a forward-rearward direction directed to the body of the subject person and is a forward movement direction when the subject person walks straight ahead. Each of the left side sensor system 101 and the right side sensor system 102 transmits the measurement data to the basal metabolism estimation device 200.

The left side sensor system 101 and the right side sensor system 102 will be generically expressed as sensor systems 100.

FIG. 1 illustrates an example in which both the left side sensor system 101 and the right side sensor system 102 are respectively provided in shoes. Shoes provided with the left side sensor system 101 and the right side sensor system 102 will be referred to as shoes 810. A shoe on the left foot side provided with the left side sensor system 101 will be referred to as a left foot shoe 811, and a shoe on the right foot side provided with the right side sensor system 102 will be referred to as a right foot shoe 812. The sensor system 100 may be provided in the shoe 810 such that it is positioned below the arch of the foot, but disposition of the sensor system 100 in the shoe 810 is not limited thereto.

Since the sensor systems 100 are provided in the shoes 810, the subject person can wear the sensor systems 100 by putting on the shoes 810. For example, in the sense that any special constitution and operation for wearing the sensor systems 100, such as separately wearing a wristband, are not required, the subject person is free from troublesomeness of wearing the sensor systems 100, and the subject person forgetting to wear the sensor systems 100 can be avoided.

In addition, since the subject person does not feel as if he/she is wearing sensors, it can be expected that the subject person will walk with a gait as in walking at a normal time. According to the basal metabolism estimation system 1, in this regard, basal metabolism can be estimated with high accuracy.

However, the sensor systems 100 are not necessarily provided in the shoes 810, and the sensor systems 100 need only be able to measure movement (particularly, an acceleration in the forward-rearward direction) of the feet of the subject person. For example, the subject person may wear the sensor systems 100 on the feet or the ankles using bands.

The basal metabolism estimation device 200 calculates basal metabolism of the subject person using the measurement data of the left side sensor system 101 and the right side sensor system 102. For example, the basal metabolism estimation device 200 receives the measurement data of the acceleration of each of the left and right feet from the left side sensor system 101 and the right side sensor system 102. Further, the basal metabolism estimation device 200 calculates the stride time index value dt and the time asymmetric index value SI on the basis of the obtained measurement data. Further, the basal metabolism estimation device 200 calculates the basal metabolism W by substituting the stride time index value dt and the time asymmetric index value SI into the foregoing Expression (5).

For example, the basal metabolism estimation device 200 is constituted using a portable computer such as a smartphone or a tablet personal computer (tablet PC). In this manner, since the basal metabolism estimation device 200 is constituted using a portable computer and the subject person carries the basal metabolism estimation device 200, the basal metabolism estimation device 200 is continuously positioned near the sensor systems 100. Accordingly, it is relatively easy for the basal metabolism estimation device 200 and the sensor systems 100 to communicate with each other, such as a case in which the basal metabolism estimation device 200 and the sensor systems 100 communicate with each other through short-range wireless communication, for example.

Figure 4:
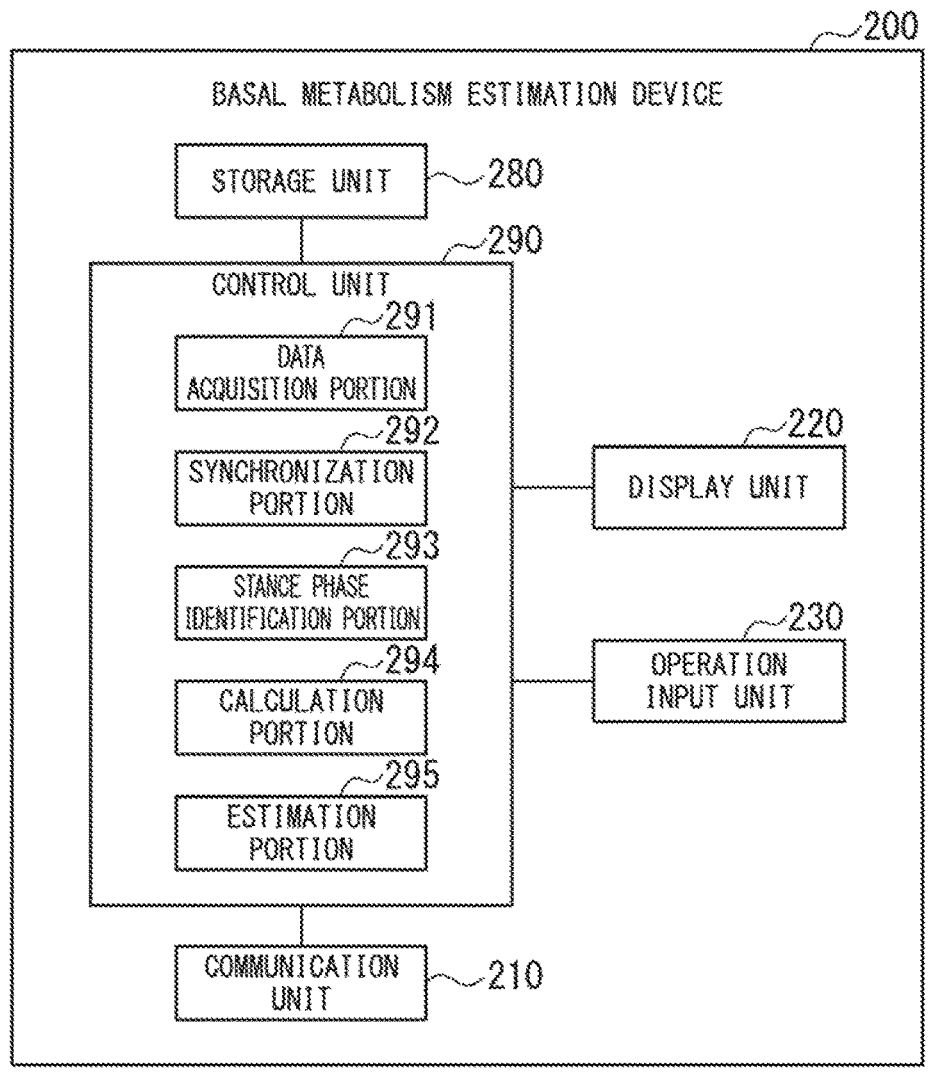
FIG. 4 is a schematic block diagram illustrating an example of a functional constitution of a basal metabolism estimation device according to the first example embodiment.

FIG. 4 is a schematic block diagram illustrating an example of a functional constitution of the basal metabolism estimation device 200. The basal metabolism estimation device 200 includes a communication unit 210, a display unit 220, an operation input unit 230, a storage unit 280, and a control unit 290. The control unit 290 includes a data acquisition portion 291, a synchronization portion 292, a stance phase identification portion 293, a calculation portion 294, and an estimation portion 295.

The communication unit 210 communicates with other devices. Particularly, the communication unit 210 communicates with the left side sensor system 101 and acquires the measurement data of the left foot. In addition, the communication unit 210 communicates with the right side sensor system 102 and acquires the measurement data of the right foot.

A communication form of the basal metabolism estimation device 200 is not limited to a particular form. For example, the basal metabolism estimation device 200 may communicate with each of the left side sensor system 101 and the right side sensor system 102 by a communication form of short-range wireless communication, but it is not limited thereto.

For example, the display unit 220 includes a display screen such as a liquid crystal panel or a light emitting diode (LED) panel, thereby displaying various images. For example, the display unit 220 displays estimation results of basal metabolism of the subject person.

However, a method by which the basal metabolism estimation device 200 outputs data is not limited to the method in which the display unit 220 displays data. For example, the communication unit 210 may transmit estimation results of basal metabolism of the subject person to other devices such as a server device.

For example, the operation input unit 230 includes an input device such as a touch sensor constituting a touch panel provided in the display screen of the display unit 220, thereby receiving an operation of a user. For example, the operation input unit 230 receives an operation of a user instructing estimation of basal metabolism.

The storage unit 280 stores various pieces of data. The storage unit 280 is constituted using a storage device included in the basal metabolism estimation device 200.

The control unit 290 performs various kinds of processing by controlling each unit of the basal metabolism estimation device 200. For example, the function of the control unit 290 is executed when a central processing unit (CPU) included in the basal metabolism estimation device 200 reads a program from the storage unit 280 and executes the program.

The data acquisition portion 291 acquires the measurement data of the acceleration of the left foot obtained by the left side sensor system 101 and the measurement data of the acceleration of the right foot obtained by the right side sensor system 102. Specifically, the data acquisition portion 291 extracts the measurement data of the acceleration of the left foot from a reception signal that is a signal received by the communication unit 210 from the left side sensor system 101. In addition, the data acquisition portion 291 extracts the measurement data of the acceleration of the right foot from a reception signal that is a signal received by the communication unit 210 from the right side sensor system 102.

The synchronization portion 292 synchronizes the measurement data of the left foot and the measurement data of the right foot with each other. Here, synchronizing the measurement data of the left foot and the measurement data of the right foot with each other indicates association between the measurement data of the left foot and the measurement data of the right foot of which at least parts of measurement periods temporally overlap each other. For example, synchronizing the measurement data of the left foot and the measurement data of the right foot with each other may be association between data for one walking cycle of the left foot and data for one walking cycle of the right foot of which parts of measurement periods overlap each other.

The stance phase identification portion 293 identifies a starting timing and an ending timing of a stance phase of each of the left and right feet from the measurement data of each of the left and right feet.

Figure 5:
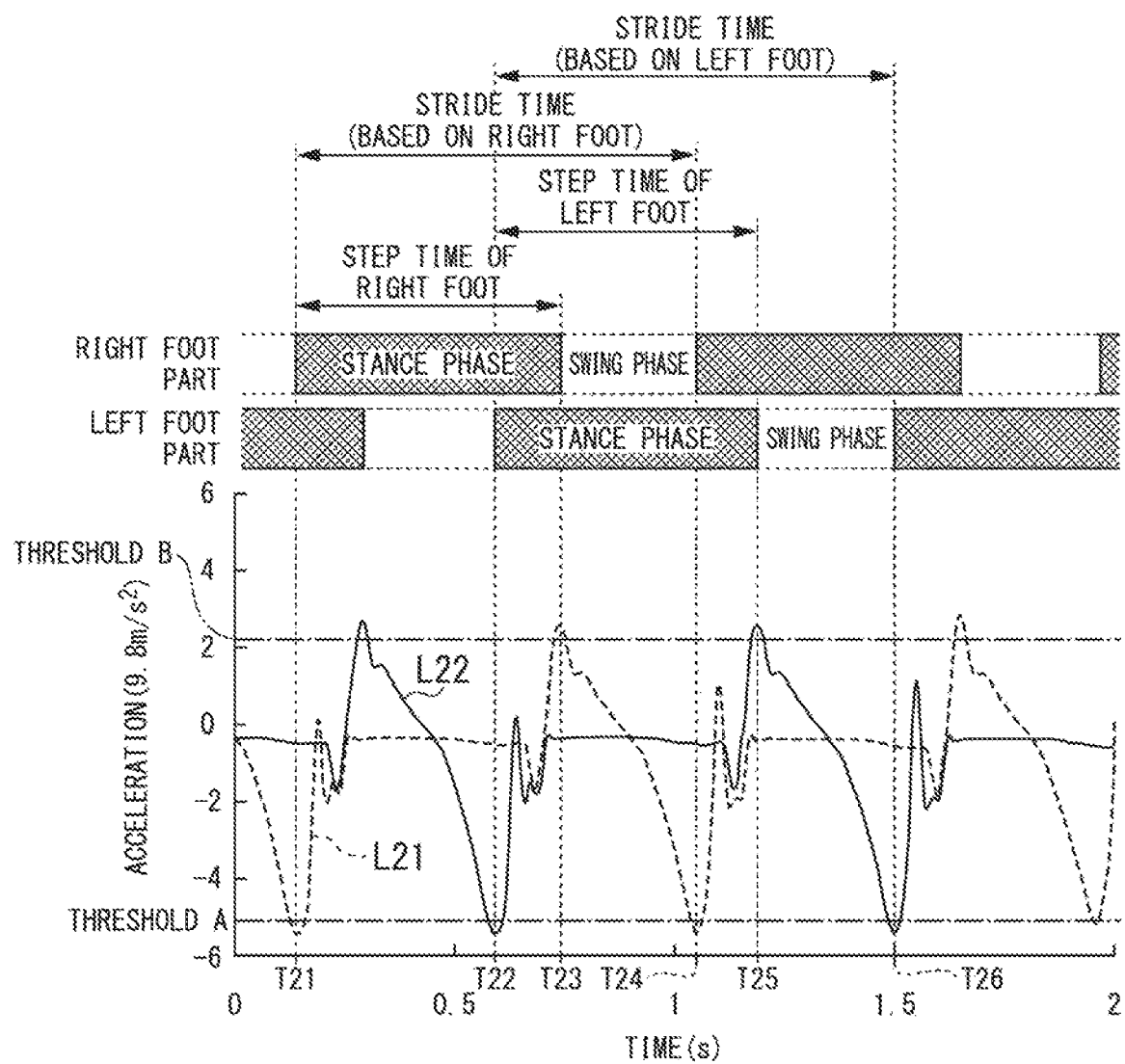
FIG. 5 is a view illustrating an example of a starting timing and an ending timing of a stance phase identified by a stance phase identification portion according to the first example embodiment.

FIG. 5 is a view illustrating an example of a starting timing and an ending timing of a stance phase identified by the stance phase identification portion 293. The horizontal axis in FIG. 5 indicates time (elapsed time from the reference time). The vertical axis indicates acceleration.

The line L21 indicates an acceleration of the right foot in the forward-rearward direction measured by the right side sensor system 102. The line L22 indicates an acceleration of the left foot in the forward-rearward direction measured by the left side sensor system 101. Both the lines L21 and L22 indicate a forward acceleration with a positive (+) value and indicate a rearward acceleration with a negative (−) value.

At a time T21, the right foot comes into contact with the ground and the stance phase of the right foot starts. At this time, the acceleration of the right foot indicated by the line L21 is extremely reduced. Since the foot swung forward from the back comes into contact with the ground surface and stops, the acceleration is decelerated in a particularly drastic manner.

At a time T22, the left foot comes into contact with the ground and the stance phase of the left foot starts. At this time, the acceleration of the left foot indicated by the line L21 becomes a local minimum (local minimum point).

At a time T23, the right foot leaves the ground, and thus the stance phase of the right foot ends and shifts to the swing phase. At this time, the acceleration of the right foot indicated by the line L21 becomes a local maximum (local maximum point). Since the foot kicks the ground surface with the toes when leaving the ground, a particularly significant acceleration is generated.

At a time T24, the right foot comes into contact with the ground again, and thus the swing phase of the right foot ends and shifts to the stance phase. Similar to the case of the time T21, the acceleration of the right foot indicated by the line L21 becomes a local minimum.

At a time T25, the left foot leaves the ground, and thus the stance phase of the left foot ends and shifts to the swing phase. Similar to the case of the right foot at the time T23, the acceleration of the left foot indicated by the line L22 becomes a local maximum. At a time T26, the left foot comes into contact with the ground again, and thus the swing phase of the left foot ends and shifts to the stance phase. Similar to the case at time T22, the acceleration of the left foot indicated by the line L22 becomes a local minimum.

The stance phase identification portion 293 identifies switching from the swing phase to the stance phase (ending of the swing phase and starting of the stance phase) by detecting a local minimum in forward acceleration regarding each of the left and right feet.

For example, the stance phase identification portion 293 may detect a timing at which a measurement value of the acceleration becomes smaller than a threshold for detecting a local minimum as a timing of switching from the swing phase to the stance phase by comparing the threshold and the measurement value to each other. A threshold for detecting a local minimum will also be expressed as a threshold A.

Alternatively, the stance phase identification portion 293 may detect a local minimum point by differentiating time series data of the measurement value of the acceleration. In this case, in order to distinguish a local minimum point at the time of switching from the swing phase to the stance phase from other local minimum points, the stance phase identification portion 293 may use both derivation and utilization of a threshold.

Specifically, when the stance phase identification portion 293 detects a local minimum point by differentiating the acceleration and a local minimum value is smaller than the threshold, a timing at which the acceleration becomes a local minimum may be detected as a timing of switching from the swing phase to the stance phase.

The threshold in this case may be a threshold (having a negative sign and a small absolute value) larger than the threshold for detecting a local minimum.

In addition, the stance phase identification portion 293 identifies switching from the stance phase to the swing phase (ending of the stance phase and starting of the swing phase) by detecting a local maximum in forward acceleration regarding each of the left and right feet.

For example, the stance phase identification portion 293 may detect a timing at which a measurement value of the acceleration becomes larger than a threshold for detecting a local maximum as a timing of switching from the stance phase to the swing phase by comparing the threshold and the measurement value to each other. A threshold for detecting a local maximum will also be expressed as a threshold B.

Alternatively, the stance phase identification portion 293 may detect a local maximum point by differentiating time series data of the measurement value of the acceleration. In this case, in order to distinguish a local maximum point at the time of switching from the stance phase to the swing phase from other local maximum points, the stance phase identification portion 293 may use both derivation and utilization of a threshold.

Specifically, when the stance phase identification portion 293 detects a local maximum point by differentiating the acceleration and a local maximum point value is larger than the threshold, a timing at which the acceleration becomes a local maximum may be detected as a timing of switching from the stance phase to the swing phase.

The threshold in this case may be a threshold larger than the threshold for detecting a local maximum indicated by the threshold B in FIG. 5 as an example.

However, data used by the stance phase identification portion 293 for identifying the starting timing and the ending timing of the stance phase is not limited to data of the acceleration of the foot in the forward-rearward direction.

For example, the data acquisition portion 291 may acquire acceleration data of the foot in an upward-downward direction regarding each of the left and right feet, and the stance phase identification portion 293 may identify the starting timing and the ending timing of the stance phase on the basis of the acceleration data of the foot in the upward-downward direction.

For example, the stance phase identification portion 293 calculates data in which a component of a gravitational acceleration is removed from the acceleration data of the foot in the upward-downward direction. Further, the stance phase identification portion 293 detects a timing switching from a state in which a downward acceleration is measured (a state in which the foot moves downward) to a state in which the measurement value of a vertical acceleration is zero (a state in which the foot does not vertically move) as a starting timing of the stance phase. In addition, the stance phase identification portion 293 detects a timing switching from a state in which the measurement value of the vertical acceleration is zero (a state in which the foot does not vertically move) to a state in which an upward acceleration is measured (a state in which the foot moves upward) as an ending timing of the stance phase.

A time period of the stance phase (a time period from the starting timing of the stance phase to the ending timing of the stance phase) detected by the stance phase identification portion 293 indicates a step time. In the example of FIG. 5, a period from the time T21 to the time T23 corresponds to the stance phase of the right foot. The stance phase identification portion 293 may calculate the period from the time T21 to the time T23 as a step time of the right foot. In addition, a period from the time T22 to the time T25 corresponds to the stance phase of the left foot. The stance phase identification portion 293 may calculate the time period from the time T22 to the time T25 as a step time of the right foot.

In addition, a combined time period of the stance phase and the swing phase detected by the stance phase identification portion 293 (a time period from the starting timing of the stance phase to the starting timing of the next stance phase) indicates a stride time. In the example of FIG. 5, a period from the time T21 to the time T24 corresponds to a stride time in a case based on a timing related to the right foot. The stance phase identification portion 293 may calculate the time period from the time T21 to the time T24 as a stride time. In addition, a period from the time T22 to the time T26 corresponds to a stride time in a case based on a timing related to the left foot. The stance phase identification portion 293 may calculate the time period from the time T22 to the time T26 as a stride time.

One walking cycle in a case based on a timing related to the right foot will also be referred to as one walking cycle of the right foot. A time period of one walking cycle of the right foot will also be referred to as a stride time of the right foot. One walking cycle in a case based on a timing related to the left foot will also be referred to as one walking cycle of the left foot. A time period of one walking cycle of the left foot will also be referred to as a stride time of the left foot.

When the subject person walks with a constant rhythm, the stride time of the right foot and the stride time of the left foot become approximately the same time.

For example, the synchronization portion 292 associates the measurement data, such as the measurement data of the right foot during the period from the time T21 to the time T23 which is a stance phase of the right foot and the measurement data of the left foot during the period from the time T22 to the time T25 which is a stance phase of the left foot, of which at least part of the measurement periods overlap each other.

For instance, when a measurement time of the measurement data of the left foot and a measurement time of the measurement data of the right foot significantly differ from each other, for example, it is conceivable that the step time differ due to a difference of a walking speed or the like. For example, regarding the time of measuring the left foot, a case in which the step time of the left foot and the step time of the right foot are substantially similar to each other and thus the value of the time asymmetric index value SI should be small is considered. In this case, since the step time differs between the left and right feet due to a difference between measuring times of the left and right feet, there is a likelihood that the value of the time asymmetric index value SI calculated by the basal metabolism estimation device 200 may increase. Due to accuracy of the time asymmetric index value SI calculated by the basal metabolism estimation device 200 being low, estimation accuracy of basal metabolism becomes also low.

In contrast, the basal metabolism estimation device 200 can calculate the time asymmetric index value SI with higher accuracy using the measurement data (measurement data synchronized by the synchronization portion 292) associated between the left and right feet. Accordingly, it is expected that basal metabolism can also be estimated with higher accuracy.

The calculation portion 294 calculates the stride time for one cycle of movement of the feet during walking and the degree of asymmetry in the left and right feet regarding the measurement data during the stance phase. In the first example embodiment, the calculation portion 294 calculates a degree of the difference between the lengths of the step times in the left and right feet as the degree of asymmetry in the left and right feet regarding the measurement data during the stance phase.

For example, the calculation portion 294 calculates the stride time index value dt and the time asymmetric index value SI described above.

The calculation portion 294 calculates the stride time for one cycle of movement of the feet during walking and the degree of asymmetry in the left and right feet regarding the measurement data during the stance phase on the basis of data synchronized by the synchronization portion 292.

Accordingly, as described above regarding the basal metabolism estimation device 200, the calculation portion 294 can avoid deterioration in estimation accuracy of basal metabolism due to a difference between the measuring times in the left and right feet and a difference between walking forms.

The estimation portion 295 estimates basal metabolism on the basis of the stride time calculated by the calculation portion 294 and the degree of asymmetry. For example, the estimation portion 295 calculates the basal metabolism W on the basis of the foregoing Expression (5).

Next, operation of the basal metabolism estimation device 200 will be described with reference to FIGS. 6 to 8.

Figure 6:
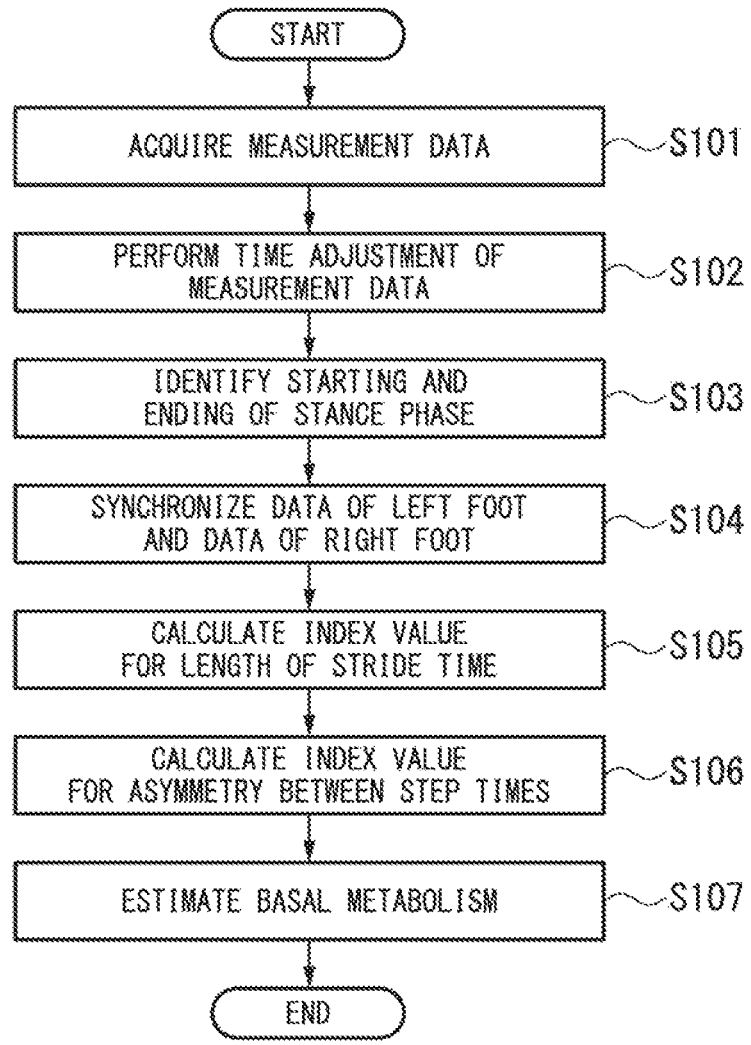
FIG. 6 is a flowchart illustrating an example of a procedure of processing in which the basal metabolism estimation device according to the first example embodiment estimates basal metabolism.

FIG. 6 is a flowchart illustrating an example of a procedure of processing in which the basal metabolism estimation device 200 estimates basal metabolism.

In the processing of FIG. 6, the data acquisition portion 291 acquires the measurement data of the left foot obtained by the left side sensor system 101 and the measurement data of the right foot obtained by the right side sensor system 102 (Step S101).

In addition, the synchronization portion 292 performs time adjustment between the measurement data of the left foot and the measurement data of the right foot (Step S102). For example, when the time (time stamp) attached to the measurement data of the left foot is delayed with respect to the time attached to the measurement data of the right foot, the synchronization portion 292 may perform time adjustment advancing the time attached to the measurement data of the left foot by the time difference.

Next, the stance phase identification portion 293 identifies the starting timing of the stance phase and the ending timing of the stance phase for each of the measurement data of the left foot and the measurement data of the right foot (Step S103). For example, as described with reference to FIG. 5, the stance phase identification portion 293 may identify the starting timing of the stance phase by comparing the measurement value of the forward acceleration and the threshold for detecting a local minimum to each other. In addition, the stance phase identification portion 293 may identify the ending timing of the stance phase by comparing the measurement value of the forward acceleration and the threshold for detecting a local maximum to each other.

Through the processing of Step S103, the measurement data is divided into pieces of data for each walking cycle. For example, the measurement data of the left foot during a period from the starting timing of the stance phase of the left foot to the starting timing of the next stance phase can be used as the measurement data for one walking cycle of the left foot. The measurement data of the right foot during a period from the starting timing of the stance phase of the right foot to the starting timing of the next stance phase can be used as the measurement data for one walking cycle of the right foot.

Next, the synchronization portion 292 synchronizes the measurement data for one walking cycle of the left foot and the measurement data for one walking cycle of the right foot with each other (Step S104). For example, as described with reference to FIG. 5, the synchronization portion 292 may synchronize the measurement data for one walking cycle of the left foot and the measurement data for one walking cycle of the right foot starting during the period of this walking cycle of the left foot with each other (that is, associate the data for one walking cycle of the left foot and the measurement data for one walking cycle of the right foot during the period of this walking cycle of the left foot with each other).

Next, the calculation portion 294 calculates the index value for the length of the stride time (Step S105). For example, the calculation portion 294 calculates the stride time index value dt described above.

In addition, the calculation portion 294 calculates the index value for asymmetry between the step times in the left and right feet (Step S106). For example, the calculation portion 294 calculates the time asymmetric index value SI described above.

Next, the estimation portion 295 estimates basal metabolism on the basis of calculation results of the calculation portion 294 (Step S107). For example, the estimation portion 295 calculates the basal metabolism W by substituting the stride time index value dt and the time asymmetric index value SI into the foregoing Expression (5).

After Step S107, the basal metabolism estimation device 200 ends the processing of FIG. 6.

The processing procedure illustrated in FIG. 6 is an example of a procedure of processing performed by the basal metabolism estimation device 200, and a procedure of processing performed by the basal metabolism estimation device 200 is not limited thereto. For example, when the basal metabolism estimation device 200 receives the measurement data in real time from each of the left side sensor system 101 and the right side sensor system 102 and a time stamp is added by the basal metabolism estimation device 200 side, time adjustment (Step S102) of the measurement data is not necessary. Also regarding the processing described with reference to FIGS. 7 and 8, a procedure of processing performed by the basal metabolism estimation device 200 is not limited thereto.

Figure 7:
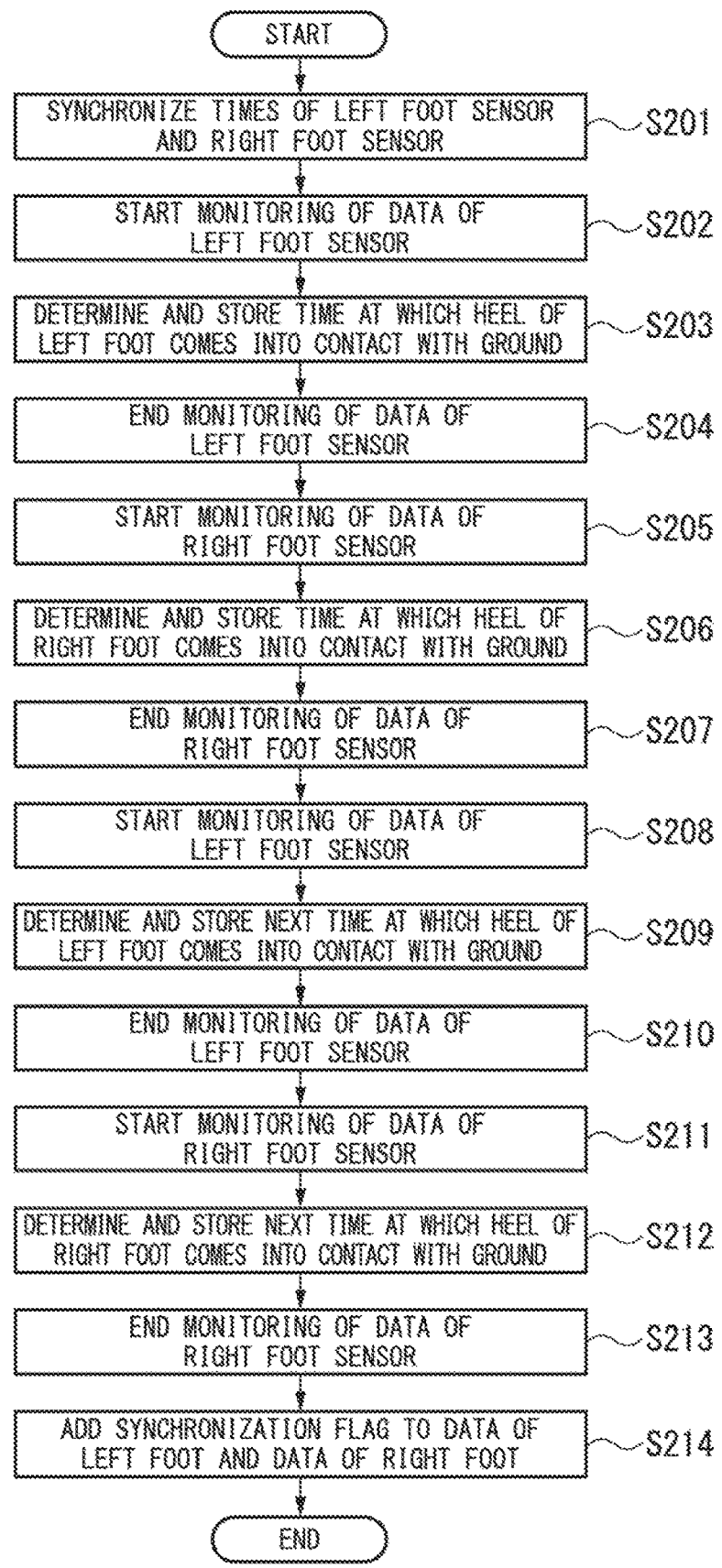
FIG. 7 is a flowchart illustrating an example of a procedure of processing in which data of a left side sensor system and data of a right side sensor system are synchronized by the basal metabolism estimation device according to the first example embodiment.

FIG. 7 is a flowchart illustrating an example of a procedure of processing in which data of the left side sensor system 101 and data of the right side sensor system 102 are synchronized by the basal metabolism estimation device 200.

In the processing of FIG. 7, the synchronization portion 292 synchronizes the time of the left side sensor system 101 and the time of the right side sensor system 102 with each other (Step S201). For example, when a timepiece (clock, watch) for a time stamp is built into each of the left side sensor system 101 and the right side sensor system 102, the synchronization portion 292 may adjust the time of the timepiece of the left side sensor system 101 and the time of the timepiece of the right side sensor system 102 to the time of the timepiece built into the synchronization portion 292 itself. Through the processing of Step S201, the time added to the measurement data of the left foot by the left side sensor system 101 and the time added to the measurement data of the right foot by the right side sensor system 102 are synchronized with each other.

Figure 8:
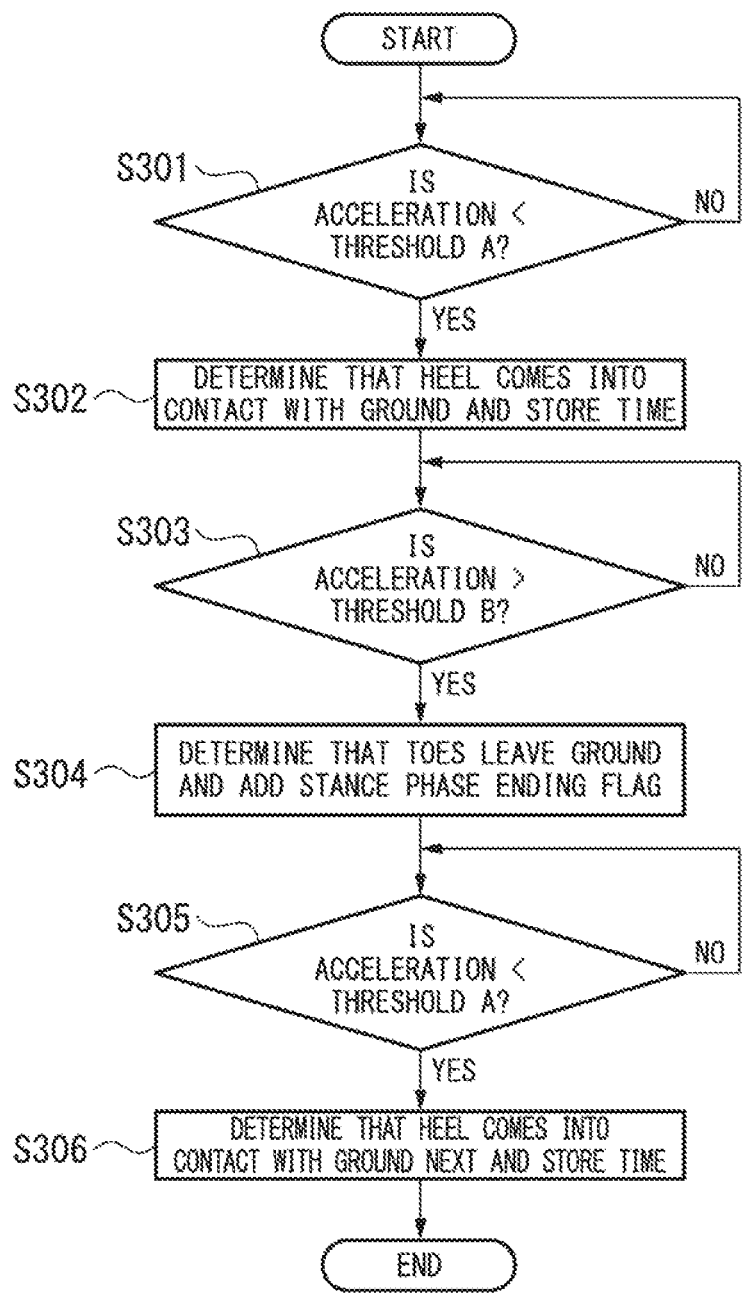
FIG. 8 is a flowchart illustrating an example of a procedure of processing in which the basal metabolism estimation device according to the first example embodiment determines the stance phases of data of the left side sensor system and data of the right side sensor system.

The processing of Step S201 corresponds to an example of the processing of Step S101 in FIG. 8.

Next, the stance phase identification portion 293 starts monitoring of the measurement data of the left foot obtained by using the left side sensor system 101 (Step S202).

Further, the stance phase identification portion 293 determines the time at which the heel of the left foot comes into contact with the ground and stores the time in the storage unit 280 as a starting time of the stance phase of the left foot (Step S203). For example, as described with reference to FIG. 5, the stance phase identification portion 293 may detect the starting time of the stance phase (the time at which the heel comes into contact with the ground) by comparing the measurement value of the forward acceleration and the threshold for detecting a local minimum to each other.

The time, at which the heel of the left foot comes into contact with the ground, determined in Step S203 will be expressed as a time T31L.

The stance phase identification portion 293, which has detected the starting time of the stance phase of the left foot in Step S203, ends monitoring of the measurement data of the left foot (Step S204) and starts monitoring of the measurement data of the right foot obtained by using the right side sensor system 102 (Step S205).

Further, the stance phase identification portion 293 determines the time at which the heel of the right foot comes into contact with the ground and stores the time in the storage unit 280 as a starting time of the stance phase of the right foot (Step S206).

The time, at which the heel of the right foot comes into contact with the ground, determined in Step S206 will be expressed as a time T31R.

The stance phase identification portion 293, which has detected the starting time of the stance phase of the right foot in Step S206, ends monitoring of the measurement data of the right foot (Step S207) and starts monitoring of the measurement data of the left foot again using the left side sensor system 101 (Step S208).

Further, the stance phase identification portion 293 determines the time at which the heel of the left foot comes into contact with the ground and stores the time in the storage unit 280 as a starting time of the stance phase of the left foot next to the stance phase of the left foot detected in Step S203 (Step S209).

The time, at which the heel of the left foot comes into contact with the ground, determined in Step S209 will be expressed as a time T41L.

The stance phase identification portion 293, which has detected the starting time of the stance phase of the left foot in Step S209, ends monitoring of the measurement data of the left foot (Step S210) and starts monitoring of the measurement data of the right foot again using the right side sensor system 102 (Step S211).

Further, the stance phase identification portion 293 determines the time at which the heel of the right foot comes into contact with the ground and stores the time in the storage unit 280 as a starting time of the stance phase of the right foot next to the stance phase of the right foot detected in Step S206 (Step S212).

The time, at which the heel of the right foot comes into contact with the ground, determined in Step S212 will be expressed as a time T41R.

The stance phase identification portion 293, which has detected the starting time of the stance phase of the right foot in Step S212, ends monitoring of the measurement data of the right foot (Step S213).

The processing from Step S202 to Step S213 corresponds to an example of processing for identifying the starting timing of the stance phase in the processing of Step S103 in FIG. 6.

Next, the synchronization portion 292 applies a synchronization flag to the data for one walking cycle of the left foot and the data for one walking cycle of the right foot (Step S214). A synchronization flag is a flag indicating that pieces of data are associated with each other through synchronization.

Specifically, the synchronization portion 292 associates the measurement data for one walking cycle of the left foot from the time T31L to the time T41L and the measurement data for one walking cycle of the right foot from the time T31R to the time T41R with each other by adding a synchronization flag.

The processing of Step S214 corresponds to an example of the processing of Step S104 in FIG. 8.

After Step S214, the basal metabolism estimation device 200 ends the processing of FIG. 7.

FIG. 8 is a flowchart illustrating an example of a procedure of processing in which the basal metabolism estimation device 200 determines the stance phases of data of the left side sensor system 101 and data of the right side sensor system 102. The basal metabolism estimation device 200 performs the processing of FIG. 8 with respect to each of the measurement data of the forward acceleration of the left foot and the measurement data of the forward acceleration of the right foot.

The processing of FIG. 8 corresponds to an example of the processing of Step S103 in FIG. 6.

In the processing of FIG. 8, the stance phase identification portion 293 refers to the measurement data in time sequence and determines whether or not the acceleration is lower than the threshold for detecting a local minimum (threshold A) (Step S301).

When the stance phase identification portion 293 determines that the acceleration is equal to or higher than the threshold for detecting a local minimum (Step S301: NO), the processing returns to Step S301.

On the other hand, when it is determined that the acceleration is lower than the threshold for detecting a local minimum (Step S301: YES), the stance phase identification portion 293 determines that it is a timing at which the heel comes into contact with the ground and stores this time in the storage unit 280 (Step S302).

Next, the stance phase identification portion 293 further refers to the measurement data in time sequence and determines whether or not the acceleration is higher than the threshold for detecting a local maximum (threshold B) (Step S303).

When the stance phase identification portion 293 determines that the acceleration is equal to or lower than the threshold for detecting a local maximum (Step S303: NO), the processing returns to Step S303.

On the other hand, when it is determined that the acceleration is higher than the threshold for detecting a local maximum (Step S303: YES), the stance phase identification portion 293 determines that it is a timing at which the toes leave the ground and adds a stance phase ending flag to the data at this time (Step S304). Alternatively, the stance phase identification portion 293 may store this time in the storage unit 280 as the ending time of the stance phase.

Next, the stance phase identification portion 293 further refers to the measurement data in time sequence and determines whether or not the acceleration is lower than the threshold for detecting a local minimum (threshold A) (Step S305).

When the stance phase identification portion 293 determines that the acceleration is equal to or higher than the threshold for detecting a local minimum (Step S305: NO), the processing returns to Step S305.

On the other hand, when it is determined that the acceleration is lower than the threshold for detecting a local minimum (Step S305: YES), the stance phase identification portion 293 determines that it is a timing at which the heel comes into contact with the ground next to the timing at which the heel comes into contact with the ground detected in Step S302 and stores this time in the storage unit 280 (Step S306).

After Step S306, the basal metabolism estimation device 200 ends the processing of FIG. 8.

Figure 9:
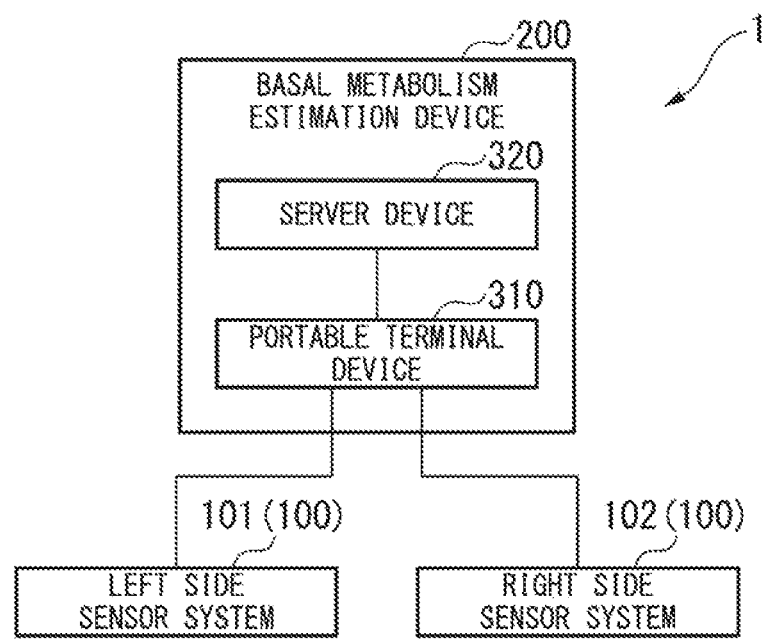
FIG. 9 is a view illustrating another example of a constitution of a basal metabolism estimation system 1 according to the first example embodiment.

FIG. 9 is a view illustrating another example of a constitution of the basal metabolism estimation system 1.

In the example of FIG. 9, the basal metabolism estimation device 200 is constituted to include a portable terminal device 310 and a server device 320.

For example, the portable terminal device 310 is equipment which can communicate with each of the left side sensor system 101, the right side sensor system 102, and the server device 320, and is, for example, a smartphone or the like.

The server device 320 is a device for executing at least some functions of the functions of the basal metabolism estimation device 200. For example, the server device 320 is constituted using a computer such as a personal computer or a workstation.

In the constitution of FIG. 9, various kinds of allotment can be adopted as allotment of the functions of the basal metabolism estimation device 200 between the portable terminal device 310 and the server device 320.

For example, the server device 320 may execute the functions of the calculation portion 294 and the estimation portion 295, and the portable terminal device 310 may execute the other functions of the basal metabolism estimation device 200. Alternatively, the portable terminal device 310 may transfer data from the left side sensor system 101 and data from the right side sensor system 102 to the server device 320 without any change, and the server device 320 may execute each of the functions of the basal metabolism estimation device 200.

As above, the data acquisition portion 291 acquires the measurement data related to each of the left and right feet. The stance phase identification portion 293 identifies the starting timing and the ending timing of the stance phase of each of the left and right feet on the basis of the measurement data acquired by the data acquisition portion 291. The calculation portion 294 calculates the stride time for one cycle of movement of the feet during walking and the degree of asymmetry in the left and right feet regarding the measurement data during the stance phase. The estimation portion 295 estimates basal metabolism on the basis of the stride time and the degree of asymmetry in the left and right feet regarding the measurement data during the stance phase.

According to the basal metabolism estimation device 200, basal metabolism can be estimated through relatively simple processing such as evaluation of the stride time and comparison of the measurement data in the left and right feet. And thus, for example, there is no need to perform complicated processing such as imaging of a physiological temperature and spatiotemporal activity heat. In this manner, according to the basal metabolism estimation device 200, metabolism can be monitored through relatively light processing. By the basal metabolism estimation device 200 estimating basal metabolism, the subject person can know basal metabolism. For example, basal metabolism can be of help to the subject person evaluating and improving his/her lifestyle and health state.

In addition, the stance phase identification portion 293 identifies the stance phase of each of the left and right feet of which parts of the measurement periods temporally overlap each other.

For instance, when a measurement time of the measurement data of the left foot and a measurement time of the measurement data of the right foot significantly differ from each other, it is conceivable that the step time differ due to a difference of a walking speed or the like, for example. For example, regarding the case of measuring the left foot, a case in which the step time of the left foot and the step time of the right foot are supposed are substantially similar to each other and thus the value of the time asymmetric index value SI should be small is considered. In this case, since the step time differs between the left and right feet due to a difference between measuring times (that is, base time of measurements) of the left and right feet, there is a likelihood that the value of the time asymmetric index value SI calculated by the basal metabolism estimation device 200 may increase. Due to accuracy of the time asymmetric index value SI calculated by the basal metabolism estimation device 200 being low, estimation accuracy of basal metabolism becomes low.

In contrast, the basal metabolism estimation device 200 can calculate the time asymmetric index value SI with higher accuracy using the measurement data (measurement data synchronized by the synchronization portion 292) associated between the left and right feet. Accordingly, it is expected that basal metabolism can also be estimated with higher accuracy.

In addition, the data acquisition portion 291 acquires the measurement data of the accelerations of the feet. The calculation portion 294 calculates the degree of asymmetry in the left and right feet regarding the step time which is a time period of the stance phase.

According to the basal metabolism estimation device 200, for example, the degree of asymmetry in the left and right feet regarding the measurement data during the stance phase can be calculated through relatively light processing such as calculation of the time asymmetric index value SI on the basis of the foregoing Expression (2).

Second Example Embodiment

Data measured by the sensor system 100 is not limited to data of accelerations of the feet. In a second example embodiment, an example in which the sensor system 100 measures a foot pressure will be described.

Here, a foot pressure indicates a pressure applied to a sole. A foot pressure is generated due to the weight supported by the foot.

The constitution of the basal metabolism estimation system 1 in the second example embodiment is similar to the constitution of the basal metabolism estimation system 1 in the first example embodiment which has been described with reference to FIG. 1. FIG. 1 will also be used in the second example embodiment, and description thereof will be omitted here.

The constitution of the basal metabolism estimation device 200 in the second example embodiment is similar to the constitution of the basal metabolism estimation device 200 in the first example embodiment which has been described with reference to FIG. 4. FIG. 4 will also be used in the second example embodiment, and description thereof will be omitted here.

Similar to the case of the first example embodiment, the constitution which has been described with reference to FIG. 9 may be applied to the basal metabolism estimation system 1 in the second example embodiment.

The second example embodiment differs from the case of the first example embodiment in that the sensor systems 100 measure foot pressures in place of accelerations of the feet. In addition, as a result, in the second example embodiment, processing performed by the stance phase identification portion 293 differs from that in the case of the first example embodiment. Except for these points, the second example embodiment is similar to the case of the first example embodiment.

Figure 10:
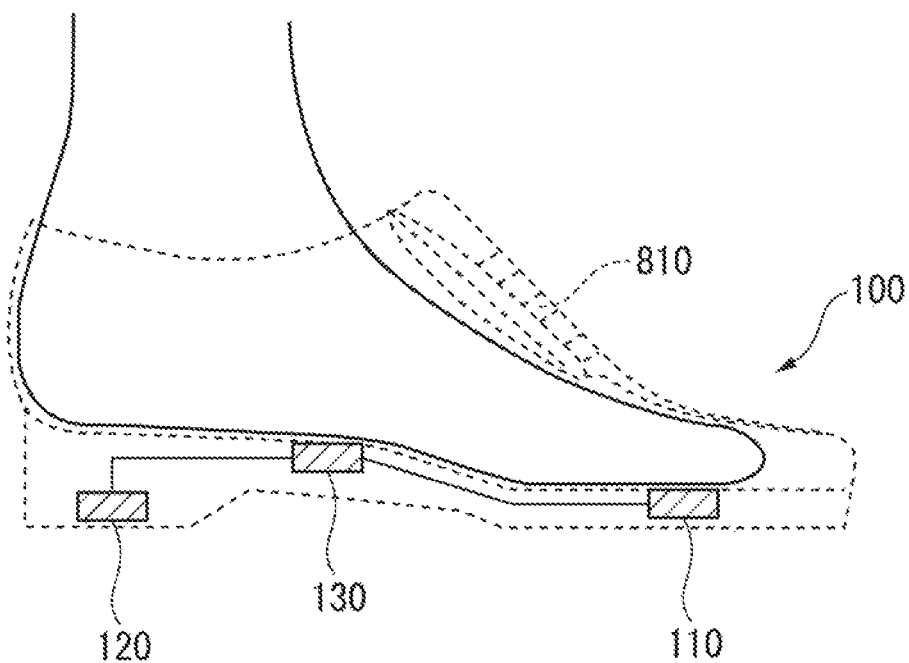
FIG. 10 is a view illustrating an example of a constitution of a sensor system according to a second example embodiment.

FIG. 10 is a view illustrating an example of a constitution of the sensor system 100. In the constitution illustrated in FIG. 10, the sensor system 100 includes a toe side sensor 110, a heel side sensor 120, and a communication device 130.

The toe side sensor 110 is provided on the toe side of the shoe 810 and measures the foot pressure on the toe side. Particularly, the toe side sensor 110 measures the foot pressure when the toes leave the ground.

The heel side sensor 120 is provided on the heel side of the shoe 810 and measures the foot pressure on the heel side. Particularly the heel side sensor 120 measures the foot pressure when the heel comes into contact with the ground.

As described above, a state in which the shoe comes into contact with the ground surface is equated with a state in which the foot comes into contact with the ground surface.

The communication device 130 communicates with other devices. Particularly, the communication device 130 transmits the measurement data of the toe side sensor 110 and the heel side sensor 120 to the basal metabolism estimation device 200.

In addition, FIG. 10 illustrates a disposition example of sensors of the sensor system 100 when the shoe 810 is viewed in a lateral direction.

In the example of FIG. 10, the toe side sensor 110 is provided on the toe side of the shoe 810 (the front side of the shoe 810), and the heel side sensor 120 is provided on the heel side of the shoe 810 (the rear side of the shoe 810). Particularly, in the example of FIG. 10, a part of the shoe 810 coming into contact with the ground is divided into the toe part on the toe side and the heel part on the heel side. The toe side sensor 110 is provided in the toe part of the shoe 810, and the heel side sensor 120 is provided in the heel part of the shoe 810.

The communication device 130 is provided between the toe part and the heel part of the shoe 810.

FIG. 10 illustrates an example of a case in which the toe side sensor 110 and the heel side sensor 120 are provided in the vicinity of a bottom surface (a surface coming into contact with the ground surface) of the shoe, but disposition of the toe side sensor 110 and the heel side sensor 120 is not limited thereto. For example, holes for respectively storing the toe side sensor 110 and the heel side sensor 120 may be provided on an upper surface (for example, immediately below an insole (shoe insert)) of a shoe sole, and the toe side sensor 110 and the heel side sensor 120 may be respectively fitted into the holes. Alternatively, the toe side sensor 110 and the heel side sensor 120 may be provided in the insole.

In addition, regarding disposition of the communication device 130, it need only be at a position where measurement data can be acquired from the toe side sensor 110 and the heel side sensor 120 and the acquired measurement data can be transmitted to the basal metabolism estimation device 200.

Figure 11:
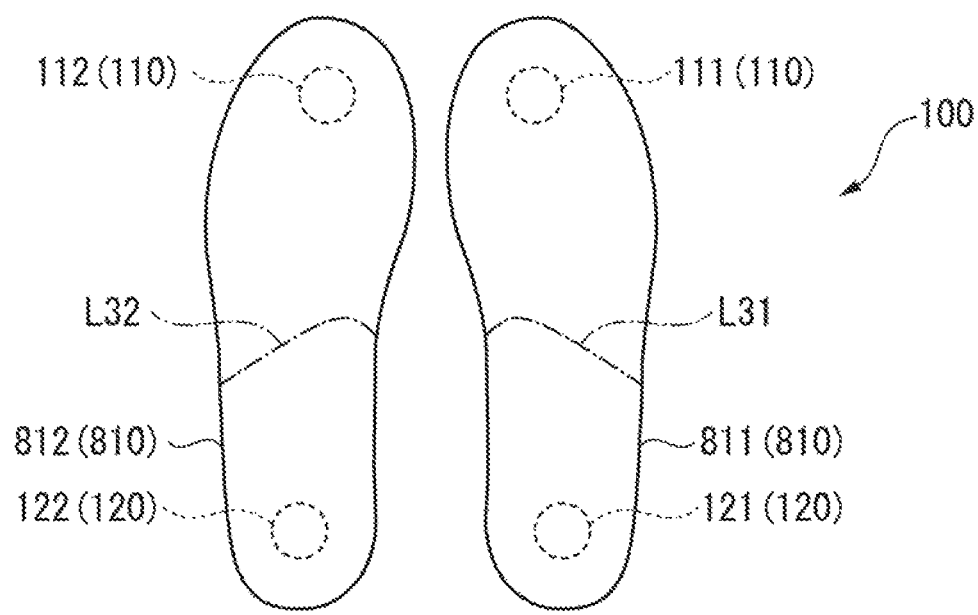
FIG. 11 is a view illustrating a disposition example of toe side sensors and heel side sensors in shoes according to the second example embodiment.

FIG. 11 is a view illustrating a disposition example of the toe side sensors 110 and the heel side sensors 120 in the shoes 810. FIG. 11 illustrates a disposition example of sensors of the sensor system 100 when the shoe 810 is viewed from the shoe sole side. That is, FIG. 11 illustrates a disposition example of sensors when the shoe sole of the shoe 810 is viewed in a manner of being looked up from the ground surface side at the time of walking.

The toe side sensor 110 installed in the left foot shoe 811 will be referred to as a left toe side sensor 111. The heel side sensor 120 installed in the left foot shoe 811 will be referred to as a left heel side sensor 121. The toe side sensor 110 installed in the right foot shoe 812 will be referred to as a right toe side sensor 112. The heel side sensor 120 installed in the right foot shoe 812 will be referred to as a right heel side sensor 122.

In the example of FIG. 11, the left foot shoe 811 and the right foot shoe 812 are divided into the toe side and the heel side respectively with lines L31 and L32 as a boundary. The left toe side sensor 111 is provided on the toe side of the left foot shoe 811. The left heel side sensor 121 is provided on the heel side of the left foot shoe 811. The right toe side sensor 112 is provided on the toe side of the right foot shoe 812. The right heel side sensor 122 is provided on the heel side of the right foot shoe 812.

Regarding setting of the toe side and the heel side of the shoe 810, they need only be set such that the toe side sensor 110 is disposed at a position where the foot pressure can be measured when the toes leave the ground and the heel side sensor 120 is disposed at a position where the foot pressure can be measured when the heel comes into contact with the ground.

For example, the toe side and the heel side of the shoe 810 may be set on the basis of the structure of the shoe 810 as in the example of FIG. 10.

Alternatively, the toe side and the heel side of the shoe 810 may be set on the basis of the structure of the foot. For example, based on a position of the arch of the sole of the foot when the subject person puts on the shoe 810, the toe side from the arch of the sole of the foot may be set as the toe side of the shoe 810, and the heel side from the arch of the sole of the foot may be set as the heel side of the shoe 810. Alternatively, based on a position of the joint part between the metatarsal bone and the tarsal bone when the subject person puts on the shoe 810, the toe side from the joint part between the metatarsal bone and the tarsal bone may be set as the toe side of the shoe 810, and the heel side from the joint part between the metatarsal bone and the tarsal bone may be set as the heel side of the shoe 810.

The number of sensors included in the sensor system 100 is not limited to two. Although, it is conceivable that accuracy of the stance phase identification portion 293 identifying the starting timing and the ending timing of the stance phase be slightly inferior, the sensor system 100 may include only one of the toe side sensor 110 and the heel side sensor 120. That is, a sensor may be provided on only one of the toe side and the heel side of the shoe 810. Accordingly, the constitution of the sensor system 100 can become a relatively simple constitution.

On the other hand, the sensor system 100 can detect a foot pressure by being provided with the toe side sensor 110 and the heel side sensor 120 as in the example of FIG. 11. In this regard, the basal metabolism estimation device 200 can estimate basal metabolism with high accuracy.

Alternatively, the sensor system 100 may include three or more sensors. Alternatively, the sensor system 100 may include one sensor capable of measuring the foot pressures on both the toe side and the heel side.

When the sensor system 100 includes the toe side sensor 110 and the heel side sensor 120, the communication device 130 may transmit the measurement data of the toe side sensor 110 and the measurement data of the heel side sensor 120 to the basal metabolism estimation device 200. Alternatively, the communication device 130 may transmit data of a summed foot pressure which is the sum of the foot pressure measured by the toe side sensor 110 and the foot pressure measured by the heel side sensor 120 to the basal metabolism estimation device 200.

Figure 12:
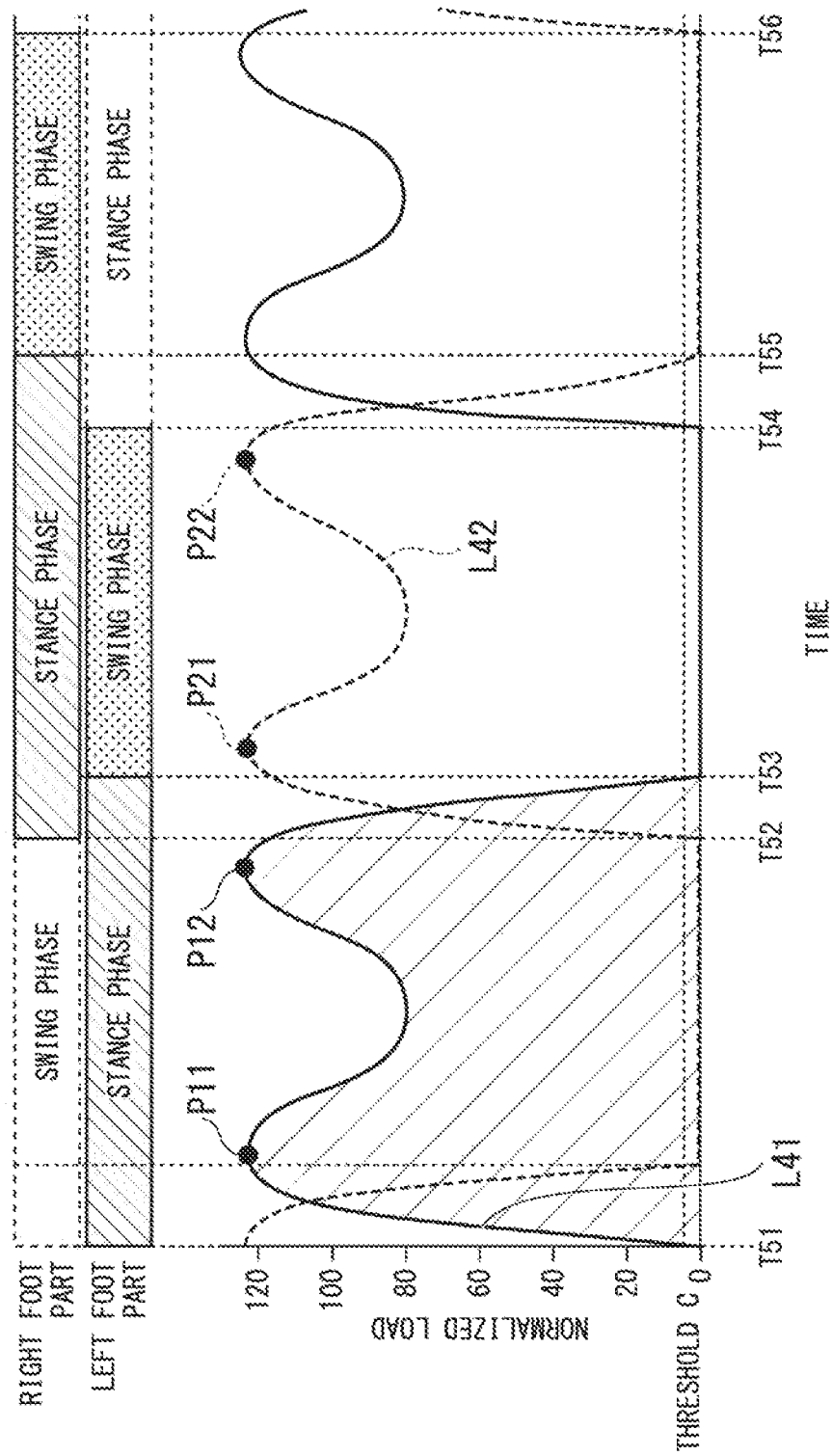
FIG. 12 is a view illustrating an example of measurement values of foot pressures obtained by the sensor system according to the second example embodiment.

FIG. 12 is a view illustrating an example of measurement values of foot pressures obtained by the sensor system 100. The horizontal axis in FIG. 12 indicates times. The vertical axis indicates measurement values of the foot pressure. The vertical axis in FIG. 12 indicates values of normalized foot pressures (normalized loads) with a reference value of the foot pressure as 100.

A line L41 indicates an example of a pressure measurement value of the left foot obtained by the left side sensor system 101. The line L41 indicates a summed value which is the sum of the foot pressure in the toes of the left foot obtained by the left toe side sensor 111 and the foot pressure in the heel of the left foot obtained by the left heel side sensor 121.

A line L42 indicates an example of a pressure measurement value of the right foot obtained by the right side sensor system 102. The line L42 indicates a summed value which is the sum of the foot pressure in the toes of the right foot obtained by the right toe side sensor 112 and the foot pressure in the heel of the right foot obtained by the right heel side sensor 122.

In the example of FIG. 12, in both the left and right feet, two local maximum points of the foot pressure are generated in one stance phase.

One of the two local maximum points is a local maximum point which is generated in the first half of the stance phase mainly by the measurement value of the heel side sensor 120. A point P11 and a point P21 correspond to examples of a local maximum point generated mainly by the measurement value of the heel side sensor 120.

The other of the two local maximum points is a local maximum point which is generated in the second half of the stance phase mainly by the measurement value of the toe side sensor 110. A point P12 and a point P22 correspond to examples of a local maximum point generated mainly by the measurement value of the toe side sensor 110.

Generally, the stance phase begins when the heel comes into contact with the ground, and the body weight is mainly applied to the heel side during the beginning of the stance phase. As the body weight applied to the foot on the opposite side is reduced, the measurement value of the foot pressure obtained by the heel side sensor 120 increases, and thus a local maximum point mainly by the measurement value of the heel side sensor 120 is generated.

Thereafter, the body weight is dispersed throughout the entire foot so that the measurement value of the foot pressure temporarily decreases.

Thereafter, as the body weight is applied to the toe side, the measurement value of the foot pressure obtained by the toe side sensor 110 increases, and thus a local maximum point is generated mainly by the measurement value of the toe side sensor 110.

Thereafter, the body weight is also applied to the foot on the opposite side (that is, the other foot), and the measurement value of the foot pressure decreases. When the toes leave the ground, the stance phase ends.

The foot pressure measured by the toe side sensor 110 and the foot pressure measured by the heel side sensor 120 may be summed on the sensor system 100 side. For example, the communication device 130 may sum the foot pressure measured by the toe side sensor 110 and the foot pressure measured by the heel side sensor 120. Alternatively, the foot pressure measured by the toe side sensor 110 and the foot pressure measured by the heel side sensor 120 may be summed on the basal metabolism estimation device 200 side. For example, the data acquisition portion 291 may sum the foot pressure measured by the toe side sensor 110 and the foot pressure measured by the heel side sensor 120.

A threshold C is a threshold used for identifying the starting timing and the ending timing of the stance phase by the stance phase identification portion 293. The stance phase identification portion 293 compares the foot pressure and the threshold C to each other and determines a timing at which the foot pressure changes from a value smaller than the threshold C to a value larger than the threshold C as the starting timing of the stance phase. In addition, the stance phase identification portion 293 determines a timing at which the foot pressure changes from a value larger than the threshold C to a value smaller than the threshold C as the ending timing of the stance phase.

In the example of FIG. 12, the foot pressure in the left foot indicated by the line L41 changes from a value smaller than the threshold C to a value larger than the threshold C at a time T51. Accordingly, the stance phase identification portion 293 determines the time T51 as the starting timing of the stance phase of the left foot.

In addition, the foot pressure in the left foot indicated by the line L41 changes from a value larger than the threshold C to a value smaller than the threshold C at a time T53. Accordingly, the stance phase identification portion 293 determines the time T53 as the ending timing of the stance phase of the left foot.

Moreover, the foot pressure in the left foot indicated by the line L41 changes from a value smaller than the threshold C to a value larger than the threshold C at a time T54. Accordingly, the stance phase identification portion 293 determines the time T54 as the starting timing of the stance phase of the left foot.

A period from the time T51 at which the stance phase of the left foot starts to the time T54 at which the stance phase of the left foot starts again corresponds to one walking cycle.

In addition, in the example of FIG. 12, the foot pressure in the right foot indicated by the line L42 changes from a value smaller than the threshold C to a value larger than the threshold C at a time T52. Accordingly, the stance phase identification portion 293 determines the time T52 as the starting timing of the stance phase of the right foot.

In addition, the foot pressure in the right foot indicated by the line L42 changes from a value larger than the threshold C to a value smaller than the threshold C at a time T55.

Accordingly, the stance phase identification portion 293 determines the time T55 as the ending timing of the stance phase of the right foot.

Moreover, the foot pressure in the right foot indicated by the line L42 changes from a value smaller than the threshold C to a value larger than the threshold C at a time T56. Accordingly, the stance phase identification portion 293 determines the time T56 as the starting timing of the stance phase of the right foot.

A period from the time T52 at which the stance phase of the right foot starts to the time T56 at which the stance phase of the right foot starts again corresponds to one walking cycle.

In one walking cycle of the left foot from a time T11L to a time T21L and one walking cycle of the right foot from a time T11R to a time T21R, periods from the time T11R to the time T21L temporally overlap each other.

For example, the stance phase identification portion 293 may cut out data for each walking cycle of the left foot from the measurement data of the foot pressure in the left foot and may cut out data for each walking cycle of the right foot from the measurement data of the foot pressure in the right foot.

Further, the synchronization portion 292 may associate (synchronize) data for one walking cycle of the left foot and data for one walking cycle of the right foot starting during this one walking cycle of the left foot with each other. For example, the synchronization portion 292 may associate the measurement data of the foot pressure in the left foot during one walking cycle of the left foot from the time T11L to the time T21L and the measurement data of the foot pressure in the right foot during one walking cycle of the right foot from the time T11R to the time T21R with each other.

One walking cycle of the left foot and one walking cycle of the right foot temporally overlap each other in the stance phase. In this regard, synchronization (association) of one walking cycle of the left foot and one walking cycle of the right foot performed by the synchronization portion 292 also corresponds to synchronization (association) of the stance phase of the left foot and the stance phase of the right foot.

The procedure of processing in which the basal metabolism estimation device 200 estimates basal metabolism is similar to the procedure of processing in the case of the first example embodiment which has been described with reference to FIG. 6 except for a difference in specific processing in which the stance phase identification portion 293 identifies the starting timing and the ending timing of the stance phase.

Regarding the processing of Step S103 in FIG. 6, in the first example embodiment, the stance phase identification portion 293 identifies the starting timing and the ending timing of the stance phase on the basis of the measurement value of the accelerations of the feet as described with reference to FIG. 5. On the other hand, in the second example embodiment, the stance phase identification portion 293 identifies the starting timing and the ending timing of the stance phase on the basis of the measurement value of the foot pressure as described with reference to FIG. 12.

A procedure of processing in which the basal metabolism estimation device 200 synchronizes data of the left side sensor system 101 and data of the right side sensor system 102 with each other is similar to the procedure of processing in the case of the first example embodiment which has been described with reference to FIG. 7 except for a difference in specific processing in which the stance phase identification portion 293 determines a time at which the heel comes into contact with the ground.

Regarding the processing of Steps S203, S206, S209 and S212 in FIG. 7, in the first example embodiment, the stance phase identification portion 293 determines a time at which the heel comes into contact with the ground on the basis of the measurement value of the accelerations of the feet as described with reference to FIG. 5. On the other hand, in the second example embodiment, the stance phase identification portion 293 determines a time at which the heel comes into contact with the ground on the basis of the measurement value of the foot pressure as described with reference to FIG. 12.

Figure 13:
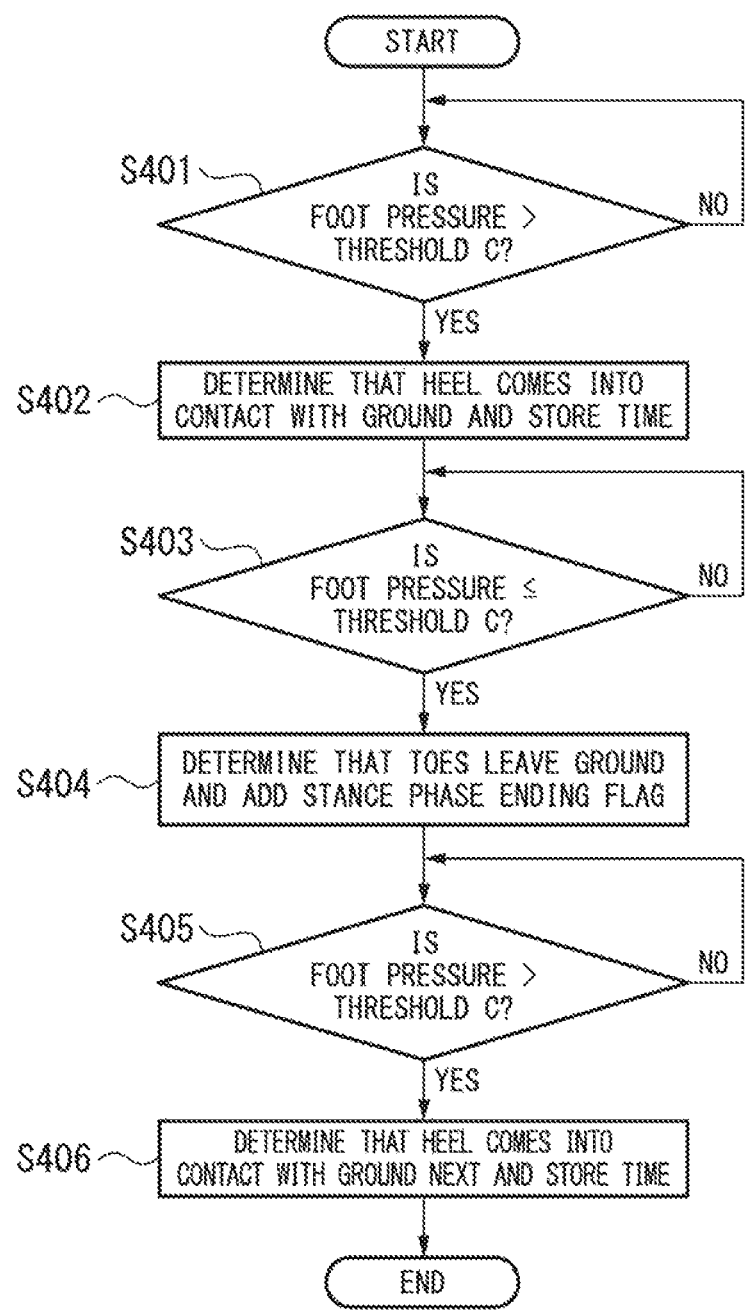
FIG. 13 is a flowchart illustrating an example of a procedure of processing in which a basal metabolism estimation device according to the second example embodiment determines the stance phases of data of the left side sensor system and data of the right side sensor system.

FIG. 13 is a flowchart illustrating an example of a procedure of processing in which the basal metabolism estimation device 200 determines the stance phases of data of the left side sensor system 101 and data of the right side sensor system 102. The basal metabolism estimation device 200 performs the processing of FIG. 13 for each of the measurement data of the foot pressure in the left foot and the measurement data of the foot pressure in the right foot.

The processing of FIG. 13 corresponds to an example of the processing of Step S103 in FIG. 6.

In the processing of FIG. 13, the stance phase identification portion 293 refers to the measurement data in time sequence and determines whether or not the foot pressure is larger than the threshold C (Step S401).

When the stance phase identification portion 293 determines that the foot pressure is equal to or smaller than the threshold C (Step S401: NO), the processing returns to Step S401.

On the other hand, when it is determined that the foot pressure is larger than the threshold C (Step S401: YES), the stance phase identification portion 293 determines that it is a timing at which the heel comes into contact with the ground and stores this time in the storage unit 280 (Step S402).

Next, the stance phase identification portion 293 further refers to the measurement data in time sequence and determines whether or not the foot pressure is smaller than the threshold C (Step S403).

When the stance phase identification portion 293 determines that the foot pressure is equal to or larger than the threshold C (Step S403: NO), the processing returns to Step S403.

On the other hand, when it is determined that the foot pressure is smaller than the threshold C (Step S403: YES), the stance phase identification portion 293 determines that it is a timing at which the toes leave the ground and adds a stance phase ending flag to the data at this time (Step S404). Alternatively, the stance phase identification portion 293 may store this time in the storage unit 280 as the ending time of the stance phase.

Next, the stance phase identification portion 293 further refers to the measurement data in time sequence and determines whether or not the foot pressure is larger than the threshold C (Step S405).

When the stance phase identification portion 293 determines that the foot pressure is equal to or smaller than the threshold C (Step S405: NO), the processing returns to Step S405.

On the other hand, when it is determined that the foot pressure is larger than the threshold C (Step S405: YES), the stance phase identification portion 293 determines that it is a timing at which the heel comes into contact with the ground next to the timing at which the heel comes into contact with the ground detected in Step S402 and stores this time in the storage unit 280 (Step S406).

After Step S406, the basal metabolism estimation device 200 ends the processing of FIG. 8.

As above, the data acquisition portion 291 acquires the measurement data of the foot pressure.

Here, generally, it is easier to make a thin pressure sensor thinner than a thin acceleration sensor. In the basal metabolism estimation system 1, in the sense that a pressure sensor is used as a sensor of the sensor system 100, the sensor can be installed in the shoe 810 in a relatively easy manner.

In addition, the calculation portion 294 calculates a degree of asymmetry in the left and right feet regarding the step time which is a time period of the stance phase.

According to the basal metabolism estimation device 200, for example, the degree of asymmetry in the left and right feet regarding the measurement data during the stance phase can be calculated through relatively light processing of calculation of the time asymmetric index value SI on the basis of the foregoing Expression (2). According to the basal metabolism estimation system 1 in the second example embodiment, basal metabolism can be estimated using a pressure sensor in place of an acceleration sensor through processing similar to the case of the basal metabolism estimation system 1 in the first example embodiment.

Third Example Embodiment

In the constitution of the second example embodiment, the basal metabolism estimation device 200 may estimate basal metabolism using a degree of asymmetry of magnitudes of the foot pressures in the left and right feet during the stance phase in place of the degree of asymmetry in the left and right feet during the step time. In a third example embodiment, this point will be described.

The constitution of the basal metabolism estimation system 1 in the third example embodiment is similar to the constitution of the basal metabolism estimation system 1 in the second example embodiment. Therefore, the constitution of the basal metabolism estimation system 1 in the third example embodiment is similar to the constitution of the basal metabolism estimation system 1 in the first example embodiment which has been described with reference to FIG. 1. FIG. 1 will also be used in the third example embodiment, and description thereof will be omitted here.

The constitution of the basal metabolism estimation device 200 in the third example embodiment is similar to the constitution of the basal metabolism estimation device 200 in the second example embodiment. Therefore, the constitution of the basal metabolism estimation device 200 in the third example embodiment is similar to the constitution of the basal metabolism estimation device 200 in the first example embodiment which has been described with reference to FIG. 4. FIG. 4 will also be used in the third example embodiment, and description thereof will be omitted here.

The constitution of the sensor system 100 in the third example embodiment is similar to the constitution of the sensor system 100 in the second example embodiment which has been described with reference to FIGS. 10 and 11. FIGS. 10 and 11 will also be used in the third example embodiment, and description thereof will be omitted here.

Similar to the cases of the first example embodiment and the second example embodiment, the constitution which has been described with reference to FIG. 9 may be applied to the basal metabolism estimation system 1 in the third example embodiment.

The third example embodiment differs from the case of the second example embodiment in that the estimation portion 295 estimates basal metabolism using a degree of asymmetry of magnitudes of the foot pressures in the left and right feet during the stance phase in place of a degree of asymmetry of the left and right feet during the step time. In addition, as a result, the third example embodiment differs from the case of the second example embodiment in that the calculation portion 294 calculates a degree of asymmetry of magnitudes of the foot pressures in the left and right feet during the stance phase in place of a degree of asymmetry of the left and right feet during the step time. Except for these points, the third example embodiment is similar to the case of the second example embodiment.

Figure 14:
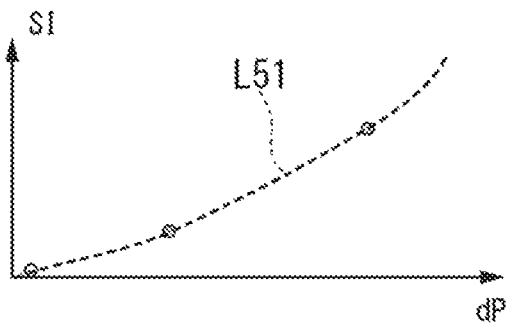
FIG. 14 is a view illustrating an example of a relationship between a degree of asymmetry of magnitudes of the foot pressures in the left and right feet during the step time and a degree of asymmetry in the left and right feet during the stance phase.

FIG. 14 is a view illustrating an example of a relationship between a degree of asymmetry in the left and right feet during the step time and a degree of asymmetry in the left and right feet regarding magnitudes of the foot pressures during the stance phase.

The horizontal axis in the graph of FIG. 14 indicates pressure asymmetric index value dP, and the vertical axis indicates time asymmetric index value SI.

The pressure asymmetric index value dP is an index value indicating a magnitude of the difference of a local maximum value of the foot pressure in the left and right feet during the stance phase. The pressure asymmetric index value dP corresponds to an example of a degree of asymmetry of magnitudes of the foot pressures in the left and right feet during the stance phase.

The pressure asymmetric index value dP is expressed by Expression (6).

$$dP = \left| \frac{P_r - P_l}{0.5 \times (P_r + P_l)} \right| \times 100\% \qquad (6)$$

The variable $P_r$ indicates a local maximum value of the foot pressure during the stance phase of the right foot. The variable $P_l$ indicates a local maximum value of the foot pressure during the stance phase of the left foot.

As the local maximum value of the foot pressure during the stance phase, a local maximum value mainly by the measurement value of the heel side sensor 120 indicated by the points P11 and P21 in FIG. 12 may be used. Alternatively, regarding the local maximum value of the foot pressure during the stance phase, a local maximum value mainly by the measurement value of the toe side sensor 110 indicated by the points P12 and P22 in FIG. 12 may be used.

Alternatively, as the local maximum value of the foot pressure during the stance phase, a largest value (maximum value) of the foot pressure during the stance phase may be used. A larger value between the local maximum value mainly by the measurement value of the heel side sensor 120 and the local maximum value mainly by the measurement value of the toe side sensor 110 corresponds to the largest value of the foot pressure during the stance phase.

The time asymmetric index value SI corresponds to an example of a degree of asymmetry in the left and right feet during the step time and is expressed by the foregoing Expression (2).

There is a positive correlation between the pressure asymmetric index value dP and the time asymmetric index value SI. That is, a relationship in which the difference between the step time of the right foot and the step time of the left foot increases as the difference between the local maximum values of the foot pressures in the right foot and the left foot increases is exhibited.

A line L51 in FIG. 14 approximately indicates a positive correlation between the pressure asymmetric index value dP and the time asymmetric index value SI by a monotonic increase function.

When a relationship between the pressure asymmetric index value dP and the time asymmetric index value SI is expressed by a function U, it is expressed by Expression (7).

$$SI=U(dP) \qquad (7)$$

Expression (8) can be obtained by substituting Expression (7) into Expression (3).

$$W=f(dt,U(dP)) \qquad (8)$$

In Expression (8), the basal metabolism W is expressed by a function of the stride time index value dt and the pressure asymmetric index value dP.

The estimation portion 295 may estimate (calculate) basal metabolism on the basis of Expression (8). In this case, the function of Expression (8) (a composite function of the function f and the function U) may be obtained through machine learning. Alternatively, a person such as a designer of the basal metabolism estimation system 1 may obtain the function of Expression (8) on the basis of statistical data, for example.

In addition, the function of Expression (8) may be obtained for each attribute of the subject person, such as each of the height, the body weight, and the age of the subject person. Further, the estimation portion 295 may estimate the basal metabolism W by acquiring the function of Expression (8) corresponding to the attribute of the subject person.

Alternatively, Expression (9) can be obtained by substituting Expression (7) into Expression (4).

$$W=g(dt)+h(U(dP)) \qquad (9)$$

In Expression (9), the basal metabolism W is expressed by the sum of a function of the stride time index value dt and a function of the pressure asymmetric index value dP.

The estimation portion 295 may estimate (calculate) basal metabolism on the basis of Expression (9). In this case, the function g and a composite function of the function f and the function U may be obtained through machine learning. Alternatively, a person such as a designer of the basal metabolism estimation system 1 may obtain the function g and a composite function of the function f and the function U on the basis of statistical data, for example.

In addition, the function g and a composite function of the function f and the function U may be obtained for each attribute of the subject person, such as each of the height, the body weight, and the age of the subject person. Further, the estimation portion 295 may estimate the basal metabolism W by acquiring the function g and a composite function of the function f and the function U corresponding to the attribute of the subject person.

Alternatively, Expression (10) can be obtained by substituting Expression (7) into Expression (5).

$$W=a \times dt^2+b \times U(dP) \qquad (10)$$

In Expression (10), the basal metabolism W is expressed by the sum of a quadratic function of the stride time index value dt and a function of the pressure asymmetric index value dP.

The estimation portion 295 may estimate (calculate) basal metabolism on the basis of Expression (9). In this case, the values of the coefficients a and b and the function U may be obtained through machine learning. Alternatively, a person such as a designer of the basal metabolism estimation system 1 may obtain the values of the coefficients a and b and the function U on the basis of statistical data, for example.

In addition, the values of the coefficients a and b and the function U may be obtained for each attribute of the subject person, such as each of the height, the body weight, and the age of the subject person. Further, the estimation portion 295 may estimate the basal metabolism W by acquiring the values of the coefficients a and b and the function U corresponding to the attribute of the subject person.

Figure 15:
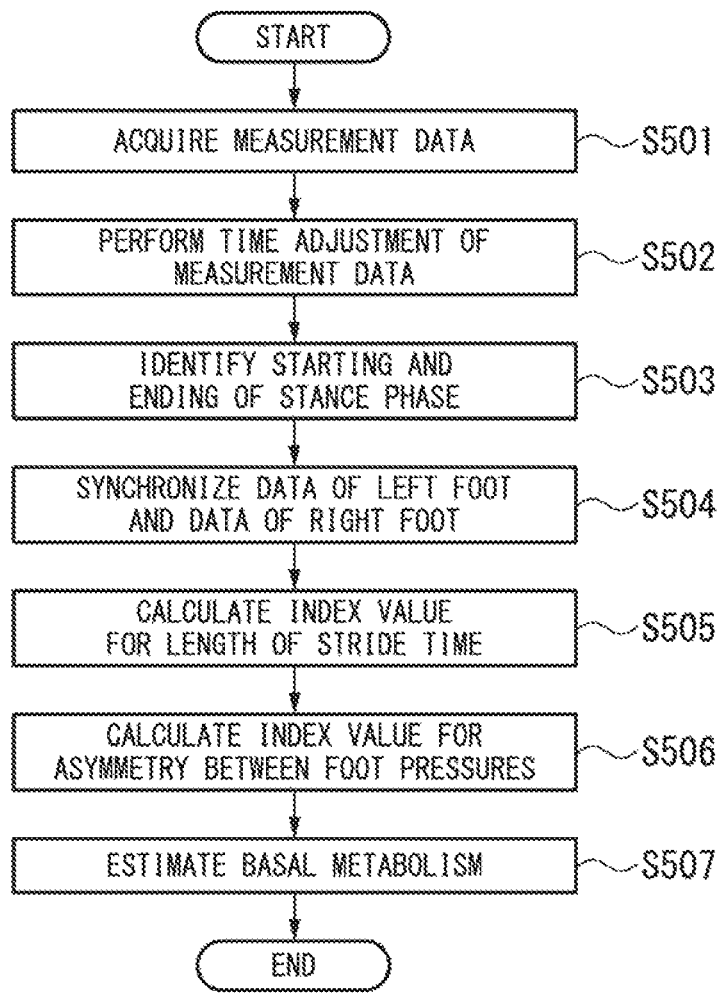
FIG. 15 is a flowchart illustrating an example of a procedure of processing in which a basal metabolism estimation device according to a third example embodiment estimates basal metabolism.

FIG. 15 is a flowchart illustrating an example of a procedure of processing in which the basal metabolism estimation device 200 estimates basal metabolism.

Steps S501 to S502 of FIG. 15 are similar to Steps S101 to S102 of FIG. 6.

Step S503 is similar to Step S103 of FIG. 6 which has been described in the second example embodiment. That is, in the first example embodiment, in Step S103 of FIG. 6, the stance phase identification portion 293 identifies the starting timing and the ending timing of the stance phase on the basis of the measurement value of the accelerations of the feet as described with reference to FIG. 5. On the other hand, in the third example embodiment, in Step S503 of FIG. 15, the stance phase identification portion 293 identifies the starting timing and the ending timing of the stance phase on the basis of the measurement value of the foot pressure as described with reference to FIG. 12.

Steps S504 to S505 are similar to Steps S104 to S105 of FIG. 6.

In Step S506, the calculation portion 294 calculates an asymmetric index value of the foot pressure. For example, the calculation portion 294 calculates the pressure asymmetric index value dP described above.

In Step S507, the estimation portion 295 estimates basal metabolism on the basis of calculation results of the calculation portion 294. For example, the estimation portion 295 calculates the basal metabolism W by substituting the stride time index value dt and the pressure asymmetric index value dP into the foregoing Expression (10).

After Step S507, the basal metabolism estimation device 200 ends the processing of FIG. 6.

The procedure of processing in which the basal metabolism estimation device 200 synchronizes (associates) data of the left side sensor system 101 and data of the right side sensor system 102 with each other is similar to the case of the second example embodiment. That is, an example of the procedure of processing in which the basal metabolism estimation device 200 synchronizes data of the left side sensor system 101 and data of the right side sensor system 102 with each other is similar to the procedure of processing in the case of the first example embodiment which has been described with reference to FIG. 7 except for a difference in specific processing in which the stance phase identification portion 293 determines a time at which the heel comes into contact with the ground.

Regarding the processing of Steps S203, S206, S209 and S212 in FIG. 7, in the first example embodiment, the stance phase identification portion 293 determines a time at which the heel comes into contact with the ground on the basis of the measurement value of the accelerations of the feet as described with reference to FIG. 5. On the other hand, in the third example embodiment, the stance phase identification portion 293 determines a time at which the heel comes into contact with the ground on the basis of the measurement value of the foot pressure as described with reference to FIG. 12.

The procedure of processing in which the basal metabolism estimation device 200 determines the stance phase of data of the left side sensor system 101 and data of the right side sensor system 102 is similar to the procedure of processing of the second example embodiment which has been described with reference to FIG. 13.

As above, the calculation portion 294 calculates a degree of asymmetry of magnitudes of the foot pressures in the left and right feet during the stance phase.

According to the basal metabolism estimation device 200, for example, the degree of asymmetry in the left and right feet regarding the measurement data during the stance phase can be calculated through relatively light processing of calculation of the pressure asymmetric index value dP on the basis of the foregoing Expression (6). Further, according to the basal metabolism estimation device 200, basal metabolism can be calculated using the degree of asymmetry in the left and right feet regarding the measurement data during the stance phase.

Figure 16:
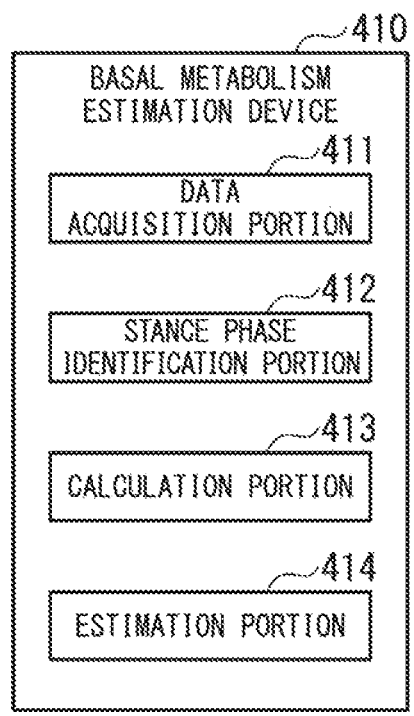
FIG. 16 is a view illustrating an example of a constitution of a basal metabolism estimation device according to an example embodiment.

FIG. 16 is a view illustrating an example of a constitution of the basal metabolism estimation device according to an example embodiment.

In the constitution illustrated in FIG. 16, a basal metabolism estimation device 410 includes a data acquisition portion 411, a stance phase identification portion 412, a calculation portion 413, and an estimation portion 414.

In this constitution, the data acquisition portion 411 acquires measurement data related to each of the left and right feet. The stance phase identification portion 412 identifies the starting timing and the ending timing of the stance phase in each of the left and right feet on the basis of the measurement data. The calculation portion 413 calculates the stride time for one cycle of movement of the feet during walking and the degree of asymmetry of the measurement data in the left and right feet during the stance phase. The estimation portion 414 estimates basal metabolism on the basis of the stride time and the degree of asymmetry.

According to the basal metabolism estimation device 410, basal metabolism can be estimated through relatively simple processing of evaluation of the stride time and comparison of the measurement data in the left and right feet. And thus, for example, there is no need to perform complicated processing such as imaging of a physiological temperature and spatiotemporal activity heat. In this manner, according to the basal metabolism estimation device 410, metabolism can be monitored through relatively light processing. By the basal metabolism estimation device 410 estimating basal metabolism, the subject person can know basal metabolism. For example, basal metabolism can be of help to the subject person evaluating and improving his/her lifestyle and health state.

Figure 17:
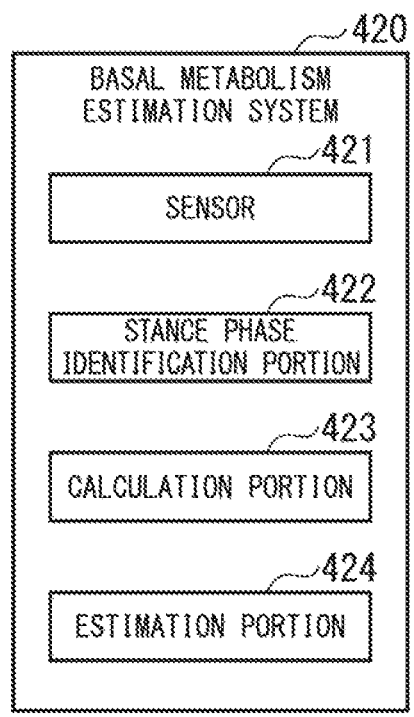
FIG. 17 is a view illustrating an example of a constitution of a basal metabolism estimation system according to an example embodiment.

FIG. 17 is a view illustrating an example of a constitution of a basal metabolism estimation system according to an example embodiment.

In the constitution illustrated in FIG. 17, a basal metabolism estimation system 420 includes a sensor 421, a stance phase identification portion 422, a calculation portion 423, and an estimation portion 424.

In this constitution, the sensor 421 measures data related to each of the left and right feet. The stance phase identification portion 422 identifies the starting timing and the ending timing of the stance phase in each of the left and right feet on the basis of the measurement data of the sensor. The calculation portion 423 calculates the stride time for one cycle of movement of the feet during walking and the degree of asymmetry of the measurement data in the left and right feet during the stance phase. The estimation portion 424 estimates basal metabolism on the basis of the stride time and the degree of asymmetry.

According to the basal metabolism estimation system 420, basal metabolism can be estimated through relatively simple processing of evaluation of the stride time and comparison of the measurement data in the left and right feet. And thus, for example, there is no need to perform complicated processing such as imaging of a physiological temperature and spatiotemporal activity heat. In this manner, according to the basal metabolism estimation system 420, metabolism can be monitored through relatively light processing.

By the basal metabolism estimation system 420 estimating basal metabolism, the subject person can know basal metabolism. For example, basal metabolism can be of help to the subject person evaluating and improving his/her lifestyle and health state.

Figure 18:
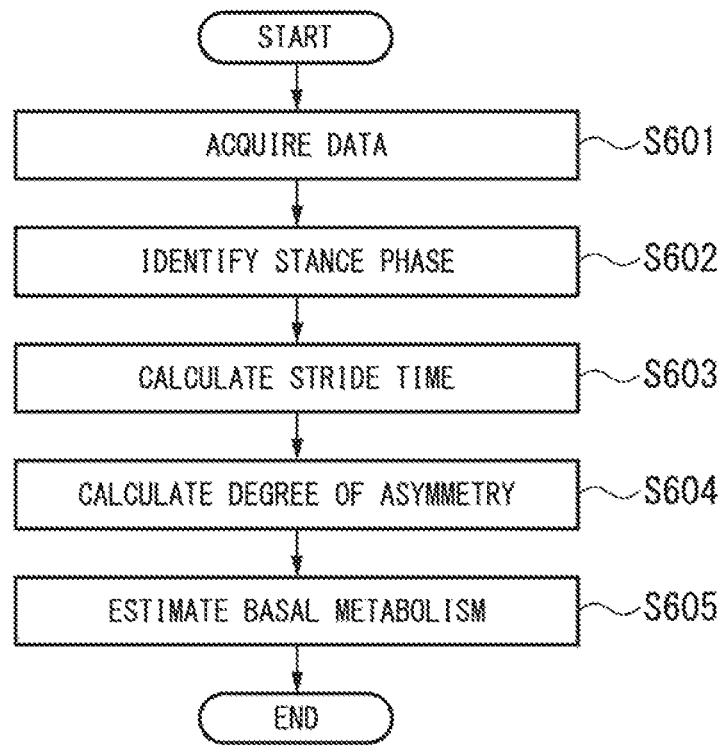
FIG. 18 is a flowchart illustrating an example of a procedure of processing in a basal metabolism estimation method of the basal metabolism estimation device according to the example embodiment.

FIG. 18 is a flowchart illustrating an example of a procedure of processing in a basal metabolism estimation method of a basal metabolism estimation device according to an example embodiment.

In the processing of FIG. 18, the basal metabolism estimation device includes a step of acquiring measurement data related to each of the left and right feet (Step S601), a step of identifying a starting timing and an ending timing of a stance phase of each of the left and right feet on the basis of the measurement data (Step S602), a step of calculating a stride time for one cycle of movement of the feet during walking and a degree of asymmetry in the left and right feet regarding the measurement data during the stance phase (Step S603), and a step of estimating basal metabolism on the basis of the stride time and the degree of asymmetry (Step S604).

According to the processing of FIG. 18, basal metabolism can be estimated through relatively simple processing of evaluation of the stride time and comparison of the measurement data in the left and right feet. And thus, for example, there is no need to perform complicated processing such as imaging of a physiological temperature and spatiotemporal activity heat. In this manner, according to the processing of FIG. 18, metabolism can be monitored through relatively light processing.

By estimating basal metabolism through the processing of FIG. 18, the subject person can know their basal metabolism. For example, basal metabolism can be of help to the subject person in evaluating and improving his/her lifestyle and health state.

Figure 19:
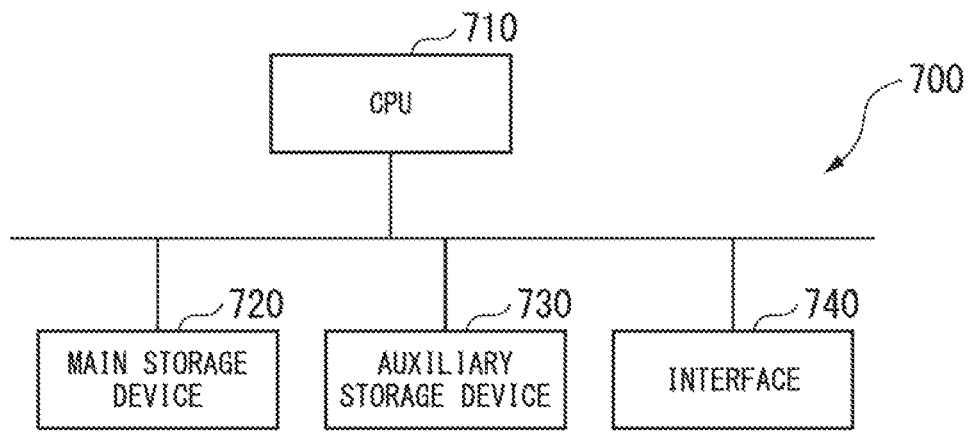
FIG. 19 is a schematic block diagram illustrating a constitution of a computer according to at least one example embodiment.

FIG. 19 is a schematic block diagram illustrating a constitution of a computer according to at least one example embodiment.

In the constitution illustrated in FIG. 19, a computer 700 includes a CPU 710, a main storage device 720, an auxiliary storage device 730, and an interface 740.

Any one of or both the basal metabolism estimation device 200 and the basal metabolism estimation device 410 may be mounted in the computer 700. In such a case, operation of each of the processing units described above is stored in the auxiliary storage device 730 in a form of a program. The CPU 710 reads the program from the auxiliary storage device 730, runs the program in the main storage device 720, and executes the foregoing processing in accordance with the program. In addition, the CPU 710 secures storage domains corresponding to the respective storage units described above in the main storage device 720 in accordance with the program. Communication between each of the devices and other devices is executed by having the interface 740 with a communication function and performing communication in accordance with control of the CPU 710.

When the basal metabolism estimation device 200 is mounted in the computer 700, operation of the control unit 290 and each unit (portion) thereof are stored in the auxiliary storage device 730 in a form of a program. The CPU 710 reads the program from the auxiliary storage device 730, runs the program in the main storage device 720 and executes the foregoing processing in accordance with the program.

In addition, the CPU 710 secures a storage domain corresponding to the storage unit 280 in the main storage device 720 in accordance with the program. Communication performed by the communication unit 210 is executed by having the interface 740 with a communication function and performing communication in accordance with control of the CPU 710. The function of the display unit 220 is executed by having the interface 740 with a display screen and displaying an image in the display screen in accordance with control of the CPU 710. The function of the operation input unit 230 is executed by having the interface 740 with an input device and receiving an operation of a user.

When the basal metabolism estimation device 410 is mounted in the computer 700, operation of the data acquisition portion 411, the stance phase identification portion 412, the calculation portion 413, and the estimation portion 414 is stored in the auxiliary storage device 730 in a form of a program. The CPU 710 reads the program from the auxiliary storage device 730, runs the program in the main storage device 720, and executes the foregoing processing in accordance with the program.

The processing of each unit (portion) may be performed by recording a program for executing all or some of the processing performed by the basal metabolism estimation device 200 and the basal metabolism estimation device 410 in a computer readable recording medium and causing a computer system to read and execute the program recorded in this recording medium. Here, a "computer system" includes an OS and hardware such as peripheral equipment.

In addition, a "computer readable recording medium" indicates a portable medium such as a flexible disk, a magneto-optical disc, a read only memory (ROM), or a compact disc read only memory (CD-ROM); or a storage device such as a hard disk built into a computer system. In addition, the foregoing program may be a program for realizing some of the functions described above. Moreover, it may be a program capable of realizing the functions described above in combination with a program which has already been recorded in a computer system.

According to at least one of the example embodiments, metabolism can be monitored through relatively light processing.

Hereinabove, the example embodiments of this invention have been described in detail with reference to the drawings, but specific constitutions are not limited to the example embodiments, and designs and the like within a range not departing from the gist of this invention are also included therein.

What is claimed is:

1. A basal metabolism estimation device comprising:
at least one memory configured to store instructions; and
at least one processor configured to execute the instructions to:
acquire, from at least one sensor when worn by a user, first measurement data related to a left foot and second measurement data related to a right foot;
identify a starting timing and an ending timing of a stance phase of each of the left and right feet based on the first and second measurement data;
calculate a difference between a stride time and a reference time, the stride time being a time for one cycle of movement of one of the feet during walking;
calculate a degree of asymmetry between the first measurement data in the stance phase of the left foot and the second measurement data in the stance phase of the right foot; and
calculate a value of basal metabolism based on the difference and the degree of asymmetry.

2. The basal metabolism estimation device according to claim 1, wherein the at least one processor is configured to execute the instructions to determine whether a part of the stance phase of the left foot temporally overlaps with a part of the stance phase of the right foot.

3. The basal metabolism estimation device according to claim 1,
wherein acquiring the first measurement data comprises acquiring measurement data of an acceleration of the left foot, and acquiring the second measurement data comprises acquiring measurement data of an acceleration of the right foot, and
calculating the degree of asymmetry comprises calculating a degree of asymmetry between a step time of the left foot and a step time of the right foot, the step time of the left foot being a time of the stance phase of the left foot, the step time of the right foot being a time of the stance phase of the right foot.

4. The basal metabolism estimation device according to claim 1, wherein acquiring the first measurement data comprises acquiring measurement data of a foot pressure of the left foot, and acquiring the second measurement data comprises acquiring measurement data of a foot pressure of the right foot.

5. The basal metabolism estimation device according to claim 4, wherein calculating the degree of asymmetry comprises calculating a degree of asymmetry between a step time of the left foot and a step time of the right foot, the step time of the left foot being a time of the stance phase of the left foot, the step time of the right foot being a time of the stance phase of the right foot.

6. The basal metabolism estimation device according to claim 4, wherein calculating the degree of asymmetry comprises calculating a degree of asymmetry between a magnitude of the foot pressure of the left foot in the stance phase of the left foot and a magnitude of the foot pressure of the right foot in the stance phase of the right foot.

7. The basal metabolism estimation device according to claim 1,
wherein acquiring the first measurement data and the second measurement data is based on controlling a plurality sensors comprising the at least one sensor,
wherein the plurality of sensors comprise a left foot group of sensors that, when worn by the user, acquire at least part of the first measurement data, and
wherein the plurality of sensors comprises a right foot group of sensors that, when worn by the user, acquire at least part of the second measurement data.

8. A basal metabolism estimation system comprising:
at least one sensor that, when worn by a user, measures first data related to a left foot and second data related to a right foot;
at least one memory configured to store instructions; and
at least one processor configured to execute the instructions to:

identify a starting timing and an ending timing of a stance phase of each of the left and right feet based on the first and second data;

calculate a difference between a stride time and a reference time, the stride time being a time for one cycle of movement of one of the feet during walking;

calculate a degree of asymmetry between the first data in the stance phase of the left foot and the second data in the stance phase of the right foot; and calculate a value of basal metabolism based on the difference and the degree of asymmetry.

9. The basal metabolism estimation system according to claim 8, further comprising:

a plurality of sensors comprising the at least one sensor, wherein the plurality of sensors comprise a left foot group of sensors that, when worn by the user, measure at least part of the first data, and wherein the plurality of sensors comprises a right foot group of sensors that, when worn by the user, measure at least part of the second data.

10. A basal metabolism estimation method comprising:

acquiring, from at least one sensor when worn by a user, first measurement data related to a left foot and second measurement data related to a right foot;

identifying a starting timing and an ending timing of a stance phase of each of the left and right feet based on the first and second measurement data;

calculating a difference between a stride time and a reference time, the stride time being a time for one cycle of movement of one of the feet during walking;

calculating a degree of asymmetry between the first measurement data in the stance phase of the left foot and the second measurement data in the stance phase of the right foot; and calculating a value of basal metabolism based on the difference and the degree of asymmetry.

11. The basal metabolism estimation method according to claim 10, wherein acquiring the first measurement data and the second measurement data is based on controlling a plurality sensors comprising the at least one sensor, wherein the plurality of sensors comprise a left foot group of sensors that, when worn by the user, acquire at least part of the first measurement data, and wherein the plurality of sensors comprises a right foot group of sensors that, when worn by the user, acquire at least part of the second measurement data.

* * * * *